United States Patent [19]

Price et al.

[11] Patent Number: 5,856,665
[45] Date of Patent: Jan. 5, 1999

[54] ARC LAMP STABILIZATION AND INTENSITY CONTROL FOR IMAGING MICROSCOPY

[75] Inventors: Jeffrey H. Price, 3881 Camino Lindo, San Diego, Calif. 92122; David Gough, Cardiff, Calif.

[73] Assignee: Jeffrey H. Price, San Diego, Calif.

[21] Appl. No.: 858,293

[22] Filed: May 19, 1997

Related U.S. Application Data

[63] Continuation of Ser. No. 470,766, Jun. 6, 1995, abandoned, which is a continuation of Ser. No. 302,044, Sep. 7, 1994, Pat. No. 5,548,661, which is a continuation of Ser. No. 17,321, Feb. 11, 1993, abandoned, which is a continuation of Ser. No. 729,383, Jul. 12, 1991, abandoned.

[51] Int. Cl.$^6$ ....................................................... G01J 1/32
[52] U.S. Cl. ........................................... 250/205; 315/151
[58] Field of Search .............................. 250/205; 315/151

[56] References Cited

U.S. PATENT DOCUMENTS

| | | |
|---|---|---|
| 4,561,104 | 12/1985 | Martin . |
| 4,668,618 | 5/1987 | Thornthwaite . |
| 4,695,884 | 9/1987 | Anastassiou et al. . |
| 4,700,298 | 10/1987 | Palcic et al. . |
| 4,741,043 | 4/1988 | Bacus . |
| 4,789,989 | 12/1988 | Stern et al. . |
| 4,866,785 | 9/1989 | Shibano . |
| 4,868,383 | 9/1989 | Kurtz et al. ............................ 250/228 |
| 4,887,892 | 12/1989 | Bacus . |
| 4,906,561 | 3/1990 | Thornthwaite . |
| 4,933,471 | 6/1990 | Lee . |
| 4,957,870 | 9/1990 | Lee et al. . |
| 4,959,301 | 9/1990 | Weaver et al. . |
| 4,983,359 | 1/1991 | Tomioka et al. . |
| 4,987,086 | 1/1991 | Brosnan et al. . |
| 4,998,043 | 3/1991 | Unami et al. ............................ 250/205 |
| 4,998,284 | 3/1991 | Bacus et al. . |
| 5,008,185 | 4/1991 | Bacus . |
| 5,016,823 | 5/1991 | Bacus et al. . |
| 5,018,209 | 5/1991 | Bacus . |
| 5,151,953 | 9/1992 | Landeta . |
| 5,226,107 | 7/1993 | Stern et al. . |

OTHER PUBLICATIONS

Adel S. Sedra and Kenneth C. Smith, Micro Electronic Circuits, Second Edition, 1987, pp. 517–518, Fig. 9.24.

S. Heynen, et al., "Optically Stabilized Mercury Short Arc Lamp As UV Light Source For Microscopy", SPIE vol. 2982, pp. 430–434, Feb. 1997.

Inoué, S. Video Microscopy, New York; Plenum Press, 1986, pp. 34, 126, 127, and 496, and Fig. 111–21.

R.I. Freshney, "The Transformed Phenotype", in Culture of Animal Cells, a Manual of Basic Technique, 2nd ed., New York: Alan R. Liss, pp. 197–206, 1987.

C. De Le Torre, et al., "Estimation of Chromatin Patterns at G1, S, and G2 of the Cell Cycle", Exp. Cell Res., vol. 88, pp. 171–174, 1974.

(List continued on next page.)

*Primary Examiner*—Edward P. Westin
*Assistant Examiner*—Kevin Pyo
*Attorney, Agent, or Firm*—Gray Cary Ware Freidenrich

[57] ABSTRACT

An operator independent image cytometer having a method for image segmentation. Image segmentation comprises the steps of filtering a digital image of a cellular specimen and thresholding the resultant image. In addition, the thresholding may include the sorting of features extracted from the filtered image. The present invention also includes a method for cytometer autofocus that combines the benefits of sharpening and contrast metrics. The present invention further includes an arc lamp stabilization and intensity control system. The image cytometer has broad applications in determining DNA content and other cellular measurements on as many as $10^5$ individual cells, including specimens of living cells. Image segmentation applications include PAP smear analysis and particle recognition.

14 Claims, 14 Drawing Sheets

Microfiche Appendix Included
(1 Microfiche, 43 Pages)

OTHER PUBLICATIONS

W. Sawicki, et al., "Change of Chromatin Morphology During the Cell Cycle Detected by Means of Automated Image Analysis", J. Cell Physiol., vol. 84, pp. 423–428, 1974.

F. Giroud, "Cell Nucleus Pattern Analysis: Geometric and Densitometric Featuring, Automatic Cell Phase identification", Biol. Cell., vol. 44, pp. 177–188, 1982.

E. A. Dawes, Quantitative Problems in Biochemistry, Baltimore: Williams and Wilkins, pp. 293–311, 1972.

R.I. Freshney, Culture of Animal Cells, a Manual of Basic Technique, 2nd ed., New York: Alan R Liss, Chapters 18 and 19, pp. 227–256, 1987.

B. H. Mayall, "Current Capabilities and Clinical Applications of Image Cytometry", Cytometry, Supplement 3, pp. 78–84, 1988.

E. Colomb, et al., "Cell Cycle Studies by Multiparametric Automatic Scanning of Topographically Preserved Cells in Culture", Cytometry, vol. 10, pp. 263–272, 1989.

G. Thurston, et al., "Cell Motility Measurements with an Automated Microscope System", Exp. Cell Res., vol. 165, pp. 380–390, 1986.

C.J. Cornelisse, et al., "DNA Image Cytometry on Machine–Selected Breast Cancer Cells and a Comparison Between Flow Cytometry and Scanning Cytophotometry", Cytometry, vol. 6, pp. 471–477, 1985.

S.S. Roberts, "Unfatal Vision: Image Cytometry Boosts Cancer Diagnosis", J. NIH Research, vol. 2, pp. 77–79, 1990.

C.J. Herman, et al., "Recent Progress in Clinical Quantitative Cytology", Arch. Pathol. Lab. Meth., vol. 111, pp. 505–512, 1987.

J.P.A. Baak, "Quantitative Pathology Today—A Technical View", Path. Res. Pract., vol. 182, pp. 396–400, 1987.

L. O'Gorman, et al., "A Systems for Automated Liver Tissue Image Analysis: Methods and Results", IEEE Transactions on Biomedical Engineering, vol. 32, pp. 696–706, 1985.

T. Takamatsu, et al., "Quantitative Fluorescence Image Analysis", Acta Histochem. Cytochem., vol. 19, pp. 61–71, 1986.

K.S. Fu, et al., "A Survey on Image Segmentation", Pattern Recognition, vol. 13, pp. 3–16, 1981.

C.J. Moran, "A Morphological Transformation for Sharpening Edges of Features before Segmentation", Computer Vision, Graphics and Image Processing, vol. 49, pp. 85–94, 1990.

S. Hamada, et al., "DAPI Staining Improved for Quantitative Cytofluorometry", Histochem., vol. 79, pp. 219–226, 1983.

G.L. Wied, et al., "Image Analysis in Quantitative Cytopathology and Histophathology", Human Pathology, vol. 20, pp. 549–571, 1989.

N.M. McKenna, et al., "Culturing Cells on the Microscope Stage", in Fluorescence Microscopy of Living Cells in Culture, Part A, Methods in Cell Biology, vol. 29, Y.L. Wang and D. Lansing Taylor eds., San Diego: Academic Press, pp. 195–205, 1989.

R.P. Haugland, Molecular Probes: Handbook of Fluorescent Probes and Research Chemicals, Eugene, Oregon: Molecular Probes, Inc., title page, tabel of contents, pp. 1–19, 1989.

J.H. Price, Scanning Cytometry for Cell Monolayers, Ph.D. Dissertation, Bioengineering, University of California, San Diego, Nov., 1990.

J.H. Price, et al., "Nuclear Recognition in Images of Fluorescent Stained Cell Monolayers", Presented at the International Society for Optical Engineering (SPIE), Applications of Digital Image Processing XI, Jul. 12, 1990.

K.K. Bose, et al., "Differences in the Flow and Absorbtion Cytometric DNA Distributions of Mouse Hepatocytes and Tumor Cells", Cytometry, vol. 10, pp. 388–393, 1989.

G. Brugal, et al., "A Double Scanning Microphotometer for Image Analysis: Hardware, Software and Biomedical Applications", J. Histochem. and Cytochem., vol. 27, No. 1, pp. 144–152, 1979.

S.D. Fosså, et al., "DNA Cytometry of Primary Breast Cancer", Acta path. microbiol. immunol. scand. Sect. A, 91:235–243, 1983.

Y. Moustafa, et al., Image analysis of cell proliferation and differentiation in the thymus of the newt Pleurodeles waltlii Michah. by SAMBA 200 cell image processing, Roux's Archives of Developmental Biology, © Springer–Verlag, 193: 139–148, 1984.

P.F. Mullaney, "Models for Low Resolution Slit Scan Measurements Based On High Resolution Laser Scanning Image Analysis: DNA and Nuclear Dimensions", Pattern Recognition, vol. 13, pp. 49–45, Pergamon Press Ltd., 1981.

P. Strang, et al., "Comparison Between Flow Cytometry an Single Cell Cytophotometry for DNA Content Analysis of the Uterine Cervix", Acta Radiologica Oncology 24, pp. 337–341, 1985.

Tanaka, "Cybest Model 3", Analytical & Quantitative Cytology, pp. 279–285, 1982.

P. Nickolls, et al., "Pre–Processing Of Images In An Automated Chromosome Analysis System", Pattern Recognition, pp. 219–229, 1981.

ARC LAMP STABILIZATION AND INTENSITY CONTROL FOR IMAGING MICROSCOPY

This application is a continuation of application Ser. No. 08/470,766, filed Jun. 6, 1995, now abandoned, which is a continuation of application Ser. No. 08/302,044, filed Sep. 7, 1994, now U.S. Pat. No. 5,548,661 which is a continuation of application Ser. No. 08/017,321, filed Feb. 11, 1993, which is abandoned, which was a continuation of application Ser. No. 07/729,383 filed Jul. 12, 1991, which is abandoned.

STATEMENT REGARDING GOVERNMENTAL RIGHTS

This invention was made with support from the United States Government under PHS Award/Grant No. 2 T32 HL 07089-16 awarded by the Department of Health and Human Services. The Government has certain rights in the invention.

MICROFICHE APPENDIX

A microfiche appendix containing computer source code is attached. The microfiche appendix comprises one (1) sheet of microfiche having 43 frames, including one title frame.

The microfiche appendix contains material which is subject to copyright protection. The copyright owner has no objection to the reproduction of such material, as it appears in the files of the Patent and Trademark Office, but otherwise reserves all copyright rights whatsoever.

BACKGROUND OF THE INVENTION

1. Field of the Invention

The present invention relates to image processing systems and, more particularly, to an image cytometer which performs image separation on a specimen.

2. Description of the Prior Art

An automated system for analysis of anchorage-dependent cells may contribute to improved understanding of many cellular functions. In vitro, anchorage-dependence is defined by the requirement that cells be attached to a substrate to proliferate. Many cell types exhibit anchorage-dependence and the loss of this requirement for attachment is usually associated with malignant transformation. (See, e.g., R. I. Freshney, "The Transformed Phenotype," in *Culture of Animal Cells, a Manual of Basic Technique*, 2nd ed., New York: Alan R. Liss, pp. 197–206, 1987.) In vivo, cell division, cell shape, cell migration, and control of cell growth and differentiation are all at least altered by interaction of cells with a substrate. For a fully automated cytometer to have the potential to analyze cellular parameters that depend on contact of cells with a substrate, the system would have to perform analyses in situ. The basis for such a system is analysis of images of the cells acquired from a computer-controlled microscope. The images acquired by scanning a specimen of cells would be analyzed to perform cytometry, the measurement of individual cells. The instrument that performs this task, the scanning or image cytometer, would ideally indicate: 1) the size and shape of cells, nuclei and key organelles; 2) the distributions and concentrations of important cellular substances; and 3) the organizational relationships of cells. Such an instrument should scan a specimen rapidly, nondestructively, and repeatedly to analyze the dynamics of large numbers of cells.

There are many potential applications for scanning or image cytometry. Cell division, for example, could be analyzed directly by repeatedly scanning a large population of cells as they progress through the phases of the cell division cycle. Current methods for measuring durations of the cell cycle phases include bromodeoxyuridine pulse labeling in flow cytometry and time-lapse cinematography in microscopy. Flow cytometry permits rapid analysis of large numbers of cells, but cannot repeatedly measure a given cell, and time-lapse cinematography allows repeated measurements of the same cells, but cannot be used for more than one or a few cells.

The scanning cytometer should bridge this gap, making it possible to track the lineage and cell cycle phase times of each cell in a large group, and differentiate between those that are quiescent and those that continue to divide. It should also be possible to correlate changes in nuclear size, shape and chromatin distribution with progression through the cell cycle. (See, e.g., C. De Le Torre and M. H. Navarrete, *Exp. Cell Res.* 88: 171–174, 1974; W. Sawicki, J. Rowinski and R. Swenson, *J. Cell Physiol.*, vol. 84: 423–428, 1974; F. Giroud, *Biol. Cell* 44: 177–188, 1982.) In addition to improving understanding of cell division, certain scanning cytometry measurements may be sensitive indices of cell health. If so, scanning cytometry may lead to practical, automated assays for toxins, drugs and infective agents.

A number of techniques for cell measurement have been used with limited success. For example, one may use the "metabolic rate" method disclosed by E. A. Dawes, *Quantitative Problems in Biochemistry*, Baltimore: Williams and Wilkins, pp.293–311, 1972, or the "pooled quantity" method described in R. I. Freshney, "Quantitation and Experimental Design," in *Culture of Animal Cells, a Manual of Basic Technique*, 2nd ed., New York: Alan R. Liss, pp. 227–256, 1987. These two types of techniques are used to analyze the culture as a whole. Measurement of the metabolic rate of cells by $CO_2$ production or $O_2$ consumption allows analysis of live cells without disruption, but yields no individual cell data. There are also a number of methods for measuring amounts of substances from the whole culture that require cell destruction. Such chemical methods include the modified Lowry assay for proteins and DNA extraction assays.

In addition, there are automated or semi-automated devices available for cell measurement. In these devices, such as the Coulter counter and the flow cytometer (also known as the FACS or fluorescence activated cell sorter), measurements are typically made on individual cells in suspension. The Coulter counter provides the simplest individual cell data, i.e., cell number. More advanced electronic counters also measure cell size. However, the Coulter counter tends to give a count only, and has the disadvantage of causing cellular disruption. The flow cytometer gives cell number and size, as well as the quantity of cellular substances labeled with a specific fluorescent dye. The flow cytometer provides very low spatial resolution, however, and also tends to disrupt the cell culture under examination. Finally, while both the Coulter counter and the flow cytometer provide data on individual cells, they cannot analyze cells attached to a substrate. There are many advantages to measuring cells without disturbing them in their "native" location (e.g., attached to a substrate), and these advantages are not possible with the above-noted devices.

Measurements of individual cells in situ have been performed with varying degrees of automation in microscopy. The simplest approaches, such as utilization of a hemocytometer, require the microscopist to count cells and record information by hand. More complicated techniques, made possible by modifications to the microscope, allow quantitation of specific cellular parameters.

The first measurements of specifically labeled cellular substances were performed using a photomultiplier tube. Use of a photomultiplier tube requires positioning the cell of interest under an aperture and does not allow measurements of shape and size. The combination of image analysis and microscopy yields size, shape, and pattern measurements and allows quantitation of labeled cellular substances (see, e.g., B. H. Mayall, "Current Capabilities and Clinical Applications of Image Cytometry," *Cytometry Supplement* 3: 78–84, 1988). There are numerous advantages in the added information available from microscope images, but the methods used to analyze them are generally more labor intensive, resulting in the analysis of much smaller numbers of cells than with flow cytometers or electronic counters. Standard microscopic methods of cell measurement are also impaired, in that they require significant human interaction and are thus quite slow. In addition, such methods have the further disadvantage of producing data that is quite subjective and is based on a limited number of cells.

Complete automation of image cytometry is necessary for practical analysis of large numbers of fixed cells and efficient repeated scanning of groups of live cells. A summary of some of the systems capable of fully automated measurement of cellular specimens is given in Table I, below. The first of these systems counts cell colonies and measures colony size, but returns no individual cell data. Fully automated analysis of cell motility has been implemented for both single cells and groups of cells (see, e.g., G. Thurston, et al., "Cell Motility Measurements with an Automated Microscope System," *Exp. Cell Res.* 165: 380–390, 1986). In that report, location was recorded with each scan but no attempt was made to analyze cell size or shape, or the quantity of cellular substances.

Others have reported success at determining whether or not a smear contains malignant cells with instruments capable of rapidly scanning a microscope slide. The machine diagnosis was compared with the expert opinion of a pathologist. Presumably, the machine diagnosis was based on the shape and density of the cell nuclei. Data such as DNA content and nuclear size compiled from the individual cells, however, was not presented. It is, therefore, impossible to know whether the methods used for automated cytology might be adapted to allow precise measurements of cell shape and size, or the quantity of cellular substances.

TABLE I

Previous Image Cytometry Automation

| Application | Recognition | Measurements |
|---|---|---|
| Colony Counting | computer, phase contrast | colony number, size |
| Cell Motility | computer, phase contrast | location, movement |
| Cytology | computer, fluorescence, PAP, Faulgen, etc. | malignant vs. nonmalignant |

Measurements of the cell nucleus and DNA content have been the focus of many cytometric studies because nuclear abnormalities are often associated with malignancy and because nuclear changes define the differences between the phases of the cell cycle. Other investigators have reported working with systems capable of various levels of automation for nuclear analysis. The SAMBA system has been used to measure DNA content on as many as 600 cells/experiment (see, e.g., E. Colomb, et al., *Cytometry* 10: 263–272, 1989) and the LEYTAS system has been used to measure DNA content on 100–300 cells/experiment (see, e.g., C. J. Cornelisse, et al., *Cytometry* 6: 471–477, 1985). The number of cells analyzed in these experiments is much smaller than the $10^4$–$10^5$ cells that can be analyzed in flow cytometry. A recent image cytometry review (see B. H. Mayall, *Cytometry Supplement* 3: 78–84, 1988), which presented DNA content experiments with 200 cells each, identified the necessity for operator interaction as a major impediment in the analysis of larger numbers of cells.

Image cytometry usually requires interactive selection of the objects of interest. During interactive operation a technician must either draw object borders with the aid of a digitization tablet or mouse, or utilize semi-automated techniques based on intensity thresholding and editing of incorrectly chosen objects. For example, the patent to Bacus (U.S. Pat. No. 5,018,209) discloses one such operator assisted system.

An image cytometry system that can perform nuclear analysis unattended by an operator has not yet been reported, prior to the present disclosure. Some review articles which provide a frame of reference for appreciating the improvements and novel features of the present invention are as follows: Roberts, *J. NIH Research* 2: 77 (1990); Herman, et al., *Arch. Pathol. Lab. Meth.* 111: 505 (1987); Baak, *Path. Res. Pract.* 182: 396 (1987); and Mayall, *Cytometry Supplement* 3: 78 (1988).

Accurate computer recognition of the cell nuclei in an image is the first step in fully automated measurement of DNA content and nuclear size, shape and pattern. In an image of cells stained with a fluorescent dye specific for DNA, computer recognition consists of correctly segmenting the image into bright foreground objects and dark background. There are many examples of image segmentation or cell edge finding techniques used for computerized recognition (see, e.g., L. O'Gorman, et al., *IEEE Transactions on Biomedical Engineering* 32: 696–706, 1985). It is difficult, however, to compare the performance of these different techniques because each method was developed for a specific application and demonstrated on only one or a few images. An assessment of the reliability of these techniques on large numbers of cells, with presentation of measurements such as DNA content, was not provided. The simplest of these methods, intensity thresholding, has been evaluated for measurement of the DNA content of fluorescent stained smears (see, e.g., T. Takamatsu, et al., *Acta Histochem. Cytochem.* 19: 61–71, 1986.). Thresholding resulted in lower precision than attained by flow cytometry. In that report, unreliable recognition was identified as a probable source of error.

In the field of image processing, image segmentation, i.e., the automated separation of objects from a background in a digital image, is a recurring theme. Previous methods for image segmentation, or object recognition, have included thresholding (or clustering), edge detection and region extraction (K. S. Fu and J. K. Mui, "A Survey on Image Segmentation", *Pattern Recognition*, vol. 13, pp. 3–16, 1981).

In thresholding, the computer utilizes differences in image intensity to delineate features from a background. In its simplest form, the image is thresholded into two intensity ranges. All pixels (or picture elements) below the threshold intensity value are separated into one group while all those equal to or above that value are separated into a second group. In more complicated methods, multiple thresholds are used and the threshold values are determined by a method called "clustering." Each set of intensity ranges can be used to identify a different type of object if intensity differences are well defined. Difficulties arise when the objects contain a broad range of intensities, or when object edges are characterized by gradual, rather than abrupt changes from internal intensity to background intensity.

In edge detection, the edges of the objects are assumed to occur where there are large changes in intensity within a short distance (small neighborhood of pixels) in the image. These steep intensity gradients can be enhanced by edge filters (convolution or Fourier). After the filter is applied, the edges appear either as white pixels on a black background or black pixels on a white background. Thresholding can then be used by a processor to locate the edge pixels. These edge pixels must then be connected by the processor and sorted to form separate boundary representations of each individual object in an image. The most complicated (and processor intensive) step involves connecting the edge pixels into continuous boundaries. In many objects, filtering results in disconnected and spotty edges that are difficult to connect and sometimes result in the joining of separate but close proximity objects. One such edge detection system was disclosed by Martin (U.S. Pat. No. 4,561,104).

Region extraction methods depend on searching sets of image pixels for similarities and grouping them according to predetermined criteria. This method sequentially searches arbitrary regions of the image for similarities or differences. If two adjacent regions are similar they are merged and if a single region is found to contain too much variability it is divided. Region merging and/or division is carried out repeatedly until the algorithm determines that the image has been segmented as well as possible. The difficulty with this method is in finding similarity criteria for grouping that can be easily implemented by computer. The other problem is that the repeating (iterative) nature of these methods can make them too slow for all but the fastest, most expensive computers.

In addition, image segmentation would be enhanced if an image cytometer had a stable source of light. Arc lamps are known to emit intensity that varies. Some of this time varying intensity is due to arc wander. Arc wander means that the source of the luminescence changes position with time. Arc wander causes the light cast on the microscope specimen to change intensity in a way that depends on the location within the microscope field of view. This means that one spot in the microscope field can increase in intensity while another spot simultaneously decreases in intensity. Due to this spatially dependent intensity variation it is not possible to place a light measuring device, such as a photodiode, at any one place in the light beam and utilize its signal to correct for intensity variation. It has been previously observed (G. W. Ellis, "Microscope Illuminator with Fiber Optic Source Integrator," *J. Cell Biol.* 101:83a, 1985) that placing an optical fiber in the microscope light path scrambles the light so that spatially dependent variation no longer exists.

Another problem with fluorescence microscopes, however, is the accumulation of enough light to cause a visible fluorescence in the specimen to be studied. Specially designed, aberration corrected optical elements are usually used to transfer illumination from an arc lamp to the microscope field. Because light transmission in optical fibers is not perfect, use of a fiber-optic light scrambler, such as an optical fiber in the light path of the microscope, further decreases the amount of light available for fluorescence excitation.

Light measurement in fluorescence image cytometry is also prone to error because current camera and image processor systems acquire and operate on 8-bit images. An 8-bit intensity measurement incorporates 256 discrete intensity values, 0 through 255. This is not enough to encompass the entire range of intensity found in an image of fluorescent-stained cell nuclei. In practice, some intensities in the brightest nuclei are actually greater than 255 and these values are incorrectly recorded as 255. This results in an underestimation of some of the integrated intensity measurements by the instrument. One way to correct this problem is to decrease the light intensity by a known amount and remeasure the portion of the microscope field that was too bright. This can now be done only by mechanically introducing a filter into the light path. The problem is that arc lamp intensity changes with temperature and a change in the electric current powering the arc lamp is followed by a slower change in temperature. This makes it essentially impossible to control arc lamp intensity by altering current alone.

Therefore, what is needed is a degree of automated image segmentation far greater than that achieved via use of all presently known image cytometers, including those described above. In particular, it would be desirable to analyze a significantly greater number of cells than is possible with other devices, requiring only minimal operator interaction at the very beginning of the procedure and data organization at the end, with complete operator independence during the actual measurement process. Furthermore, it would be an advantage if an image cytometer could stabilize and control the intensity of an arc lamp.

SUMMARY OF THE INVENTION

The above-mentioned needs are satisfied by the present invention which includes a method for locating objects in an image. This method utilizes a digital filter, such as convolution or Fourier, to create a second image in the computer from which objects can be recognized by thresholding an image parameter such as intensity.

The method, termed pattern filtering object detection, assures that the image objects to be detected by the computer contain certain patterns that are different from the background. Using the appropriate filter, it is possible to transform the object patterns into a high (or low) intensity and the background patterns into a low (or high) intensity. Following the conversion of the image into an intermediate, high object-to-background contrast image, thresholding is used to separate the object pixels from background pixels and the object pixels can be sorted into individual object structures in computer memory. This method has an advantage over simple edge detection because more information within the object is utilized to determine its extent than just the edge region. It also has a distinct advantage over region extraction because region similarities are enhanced in a single step, rather than a repeating, iterative fashion. Fast computer hardware for implementing convolution and Fourier filtering is just becoming inexpensive enough to make this method practical.

In Fourier spectrum terms, each object may be thought of as having a specific set of frequencies. This set of frequencies can be transformed into an image where this set of frequencies is represented by a high (or low) intensity while the background, which contains a different set of intensities, is transformed into a low (or high) intensity. The better the filter performs, the wider will be the intensity difference between the objects and background and the greater the intensity gradients at the boundaries.

If filtering does not create high enough object-to-background contrast, other methods can be used to improve image segmentation. In the implementation described here, the filter makes it possible to select each object with a single threshold but objects are sometimes different enough from each other to require different thresholds for objects in the same image. Therefore, a method for adjusting the threshold for each individual object is utilized to improve the object detection.

An additional problem arising from a less than ideal filter is the enhancement of internal edges to the degree that some pixels inside the object fall on the incorrect side of the final threshold. This problem sometimes occurs with the cell nucleus images segmented in the image cytometer application described herein. Since the pixels erroneously identified as background are always completely surrounded by object pixels, they can be corrected by a hole filling method that converts all completely enclosed background pixels into object pixels. The hole filling method is non-iterative and fast.

One goal of the present invention is the development of a system capable of unattended analysis of cell monolayers stained with a dye or other label. In one embodiment, the label is specific for DNA. In various embodiments, the label is a stain or dye; in others, it is a fluorescent dye. In preferred preparations of specimens, overlap artifacts are rare and there are few sources of nonspecific fluorescence. In addition, the cells are relatively flat, decreasing error due to limited depth of field. Along with the high contrast provided by fluorescent staining, these characteristics simplify image analysis and identification of photometric errors due directly to the instrument rather than the specimen. The discussions and data presented herein for the present image cytometer include methods for fully automated operation and precision measurement of fluorescent light.

The present invention also includes a novel arc lamp stabilization and intensity control system. It has been found that the removal of spatially dependent intensity changes by a fiber optic light scrambler also allows a photodiode-feedback circuit to be used to stabilize the remaining temporal fluctuations. This becomes possible because after the fiber optic scrambler, intensity changes in any portion of the light coincide with changes in all portions of the light.

A device for increasing the amount of light transmitted into an optical fiber is currently available. This device (Photomax arc lamp, from Oriel Corp. of Stratford, Conn.) uses an ellipsoidal mirror to collect 2–4 times as much light from an arc lamp as the lens and mirror system used in commercially available microscope arc lamp sources. Because microscopes are thought of as image forming devices, the idea of utilizing an ellipsoidal reflector in the illumination system is unconventional. However, because the optical fiber is utilized as a light scrambler, its output pattern is substantially independent of the input pattern. Therefore, the fact that the ellipsoidal reflector may have aberrations and is not a good image forming optical element is unimportant. Only the amount of light transferred to the optical fiber is important. In addition to the increased illumination with an ellipsoidal reflector, the optical configuration is simplified. While conventional microscope arc lamps require a reflecting mirror and two lens groups to focus the light onto the optical fiber, the light from the ellipsoidal reflector, as used in the present invention, focuses directly onto the optical fiber with no intervening lens elements.

In conjunction with the fiber optic light scrambler and the photodiode-feedback stabilization described above, disclosed herein is a device for electrical control of arc lamp intensity. This involves utilizing a servo controlled amplifier that matches the intensity of the lamp to a computer-controlled reference value. The servo amplifier stabilizes the light intensity by matching the voltage from the photodiode to a predetermined reference voltage. This reference voltage is controlled by the computer and can be changed to alter light intensity. It has been found that the intensity can be controlled through at least a ten-fold range without extinguishing the arc lamp.

These and other objects and features of the present invention will become more fully apparent from the following description and appended claims taken in conjunction with the accompanying drawings.

DETAILED DESCRIPTION OF THE PREFERRED EMBODIMENTS

Reference is now made to the drawings wherein like numerals refer to like parts throughout. The following detailed description is divided into four sections: The Image Cytometer, Applications of the Image Cytometer, The Arc Lamp Stabilization and Intensity Control System, and Summary.

The Image Cytometer

Figure 1:
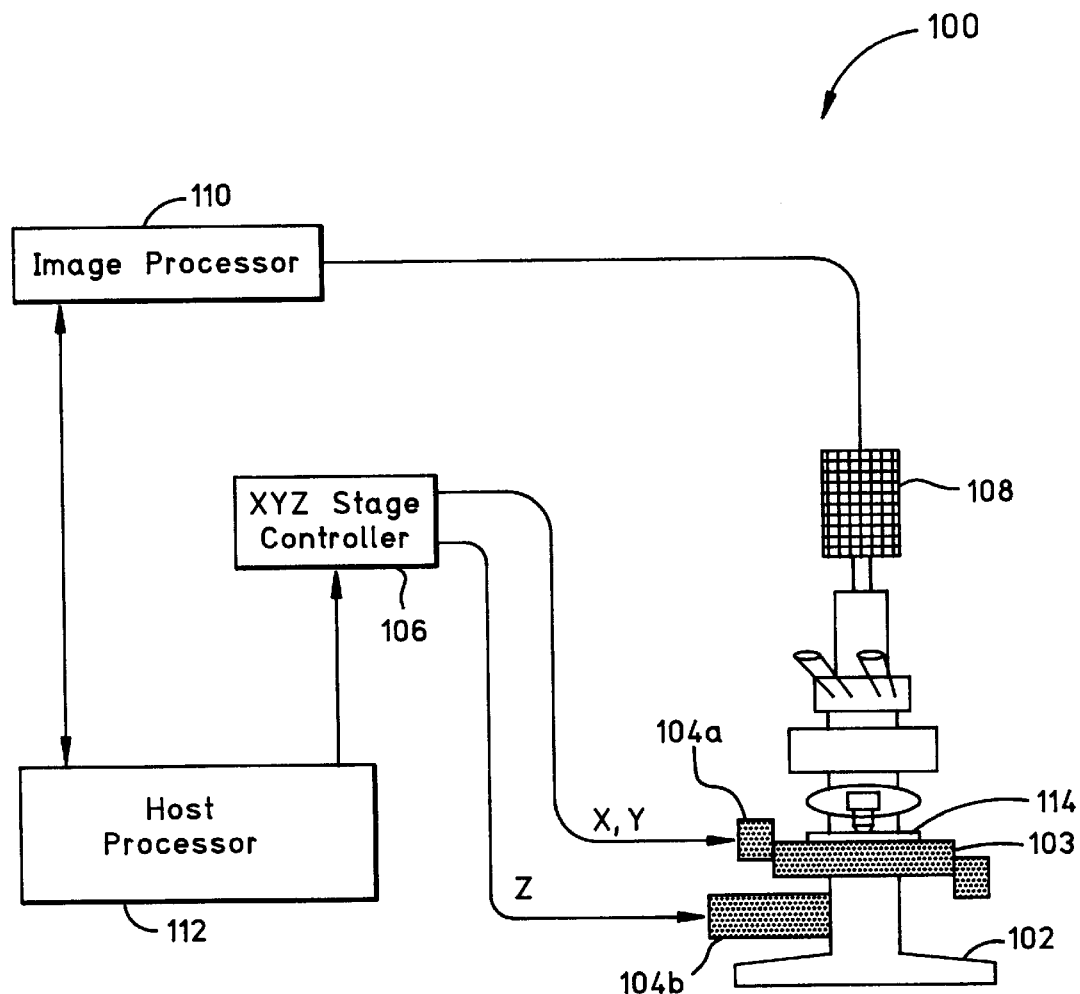
FIG. 1 is a block diagram of one presently preferred embodiment of the cytometer of the present invention.

FIG. 1 illustrates the presently preferred embodiment of an operator independent image cytometer 100 of the present invention. The hardware components of the cytometer 100 include an epifluorescent microscope 102, a motorized stage 103, controlled by a pair of XY motors 104a and a Z motor 104b, XYZ stage controller 106, a video camera 108 (preferably model NC200, Patterson Electronics of Irvine, Calif.), an image processor 110, and a host processor 112.

The microscope 102 (individual parts not shown) is preferably a Nikon Optiphot with a 100 watt mercury vapor arc lamp, a quartz collector and a 20× fluorite objective for UV fluorescent excitation. The fluorescent filter block (Omega Optical of Brattleboro, Vt.) consists of an excitation filter with a peak transmittance at 365 nanometers and a 10 nm bandwidth, a dichroic mirror that reflects below 405 nm, and a barrier filter with a peak transmittance at 485 nm and a 30 nm bandwidth.

The host processor 112 is preferably a microcomputer such as an IBM PC/AT compatible having an Intel 80286, 10 MHz, 1 wait state CPU, and a 2 Megabyte RAM memory and 80 Megabyte hard drive (not shown), available as a unit from Datel (San Diego, Calif.). The host processor 112 controls the image processor 110 (preferably a Series 151 from Imaging Technology Inc. of Woburn, Mass.) and the motorized stage 103 (such as one available from Syn-Optics of Sunnyvale, Calif.). The host processor 112 communicates with the image processor 110 via an interface board (supplied with the Series 151) that is plugged into an expansion slot in the host processor 112. The host processor 112 communicates with the stage controller 106 via a serial port to move the stage 103 in the X, Y directions for lateral positioning and the Z direction for autofocus. The stage 103 is moved under the control of the host processor 112 so that various portions or fields of a specimen 114 can be examined.

Figure 2:
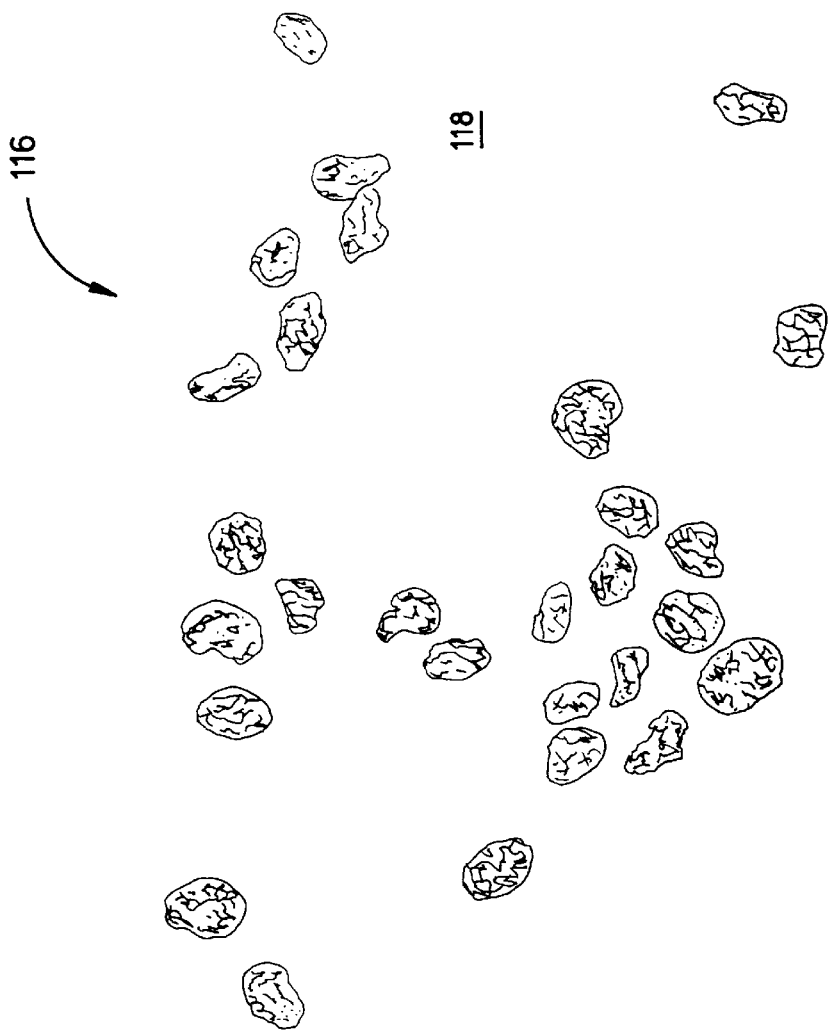
FIG. 2 is a representation of a magnified image of cells as seen through the microscope of the cytometer shown in FIG. 1.

A portion of an example specimen, such as the specimen 114 of FIG. 1, is shown in FIG. 2. FIG. 2 represents a magnified image of a specimen comprising a set of cells, particularly cell nuclei, generally indicated at 116. In this example, the cells 116 are normal neonatal foreskin fibroblasts that have been plated on a washed, autoclaved microscope slide (not shown). The cells 116 have been stained with a fluorescent staining solution as will be further discussed hereinbelow.

The fluorescent staining produces increased light intensity in the cell nuclei. The representation of FIG. 2 shows the cells, or cell nuclei 116, in a reverse or negative image as darker regions against a light background 118. However, it should be understood that the positive, or "normal", image will have the cells 116 appear as light regions against a dark background. Henceforth, a reference to an image will refer to such a normal image.

It should be noted that the cells 116 do not share the same intensity from one cell to another, or even from one point within any single cell to another. Hence, segmenting the cells 116 from the background 118 for further processing by a computer cannot be performed by using only an intensity thresholding technique.

Figure 3:
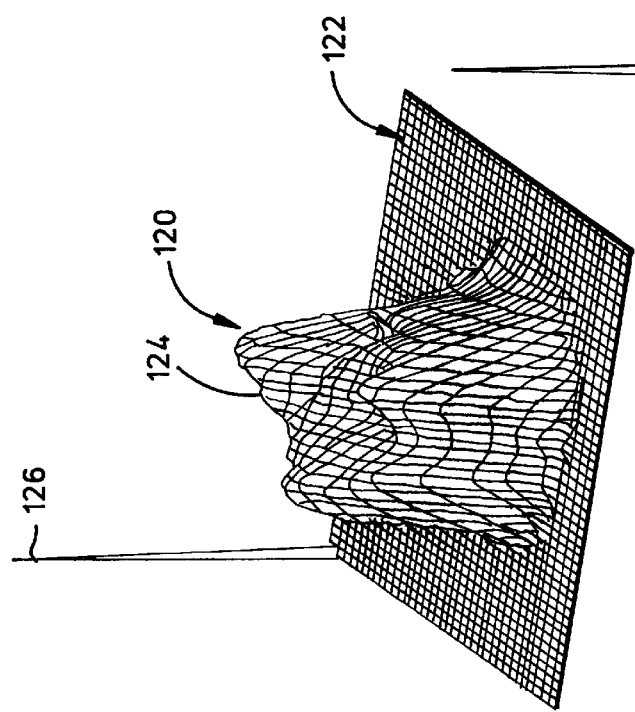
FIG. 3 is a three-dimensional plot of a gray-scale object that is representative of a cell.

FIG. 3 shows a three-dimensional plot of a gray-scale digital image of a cell (such as one of the cells 116 shown in FIG. 2, but here the cell is shown in its normal image form of higher light intensity on a lower intensity background). Note that after the image of one or more cells is received by the video camera 108 and digitized by the image processor 110, each digitized cell is then referred to as an object 120. The area surrounding the object 120 is termed a background 122.

The X, Y plane of the plot corresponds to the X, Y plane of the stage 103 (FIG. 1). The Z, or vertical, axis represents light intensity. The plot is divided into small units commonly referred to as pixels as is indicated in FIG. 3, for example, by a pixel 124. A scaling spike 126, representing maximum intensity, is located at one corner of the plot. The plot clearly shows the variation of the intensity commonly found within a single cell.

A fundamental problem that is addressed by the present invention is image separation, i.e., separating many objects, such as 120, from the image background so that the cells 116 (FIG. 2) can thereafter be analyzed by a computer. The process of image segmentation begins when the magnified image is fed from the CCD camera 108 (FIG. 1) to the image processor 110.

Figure 4:
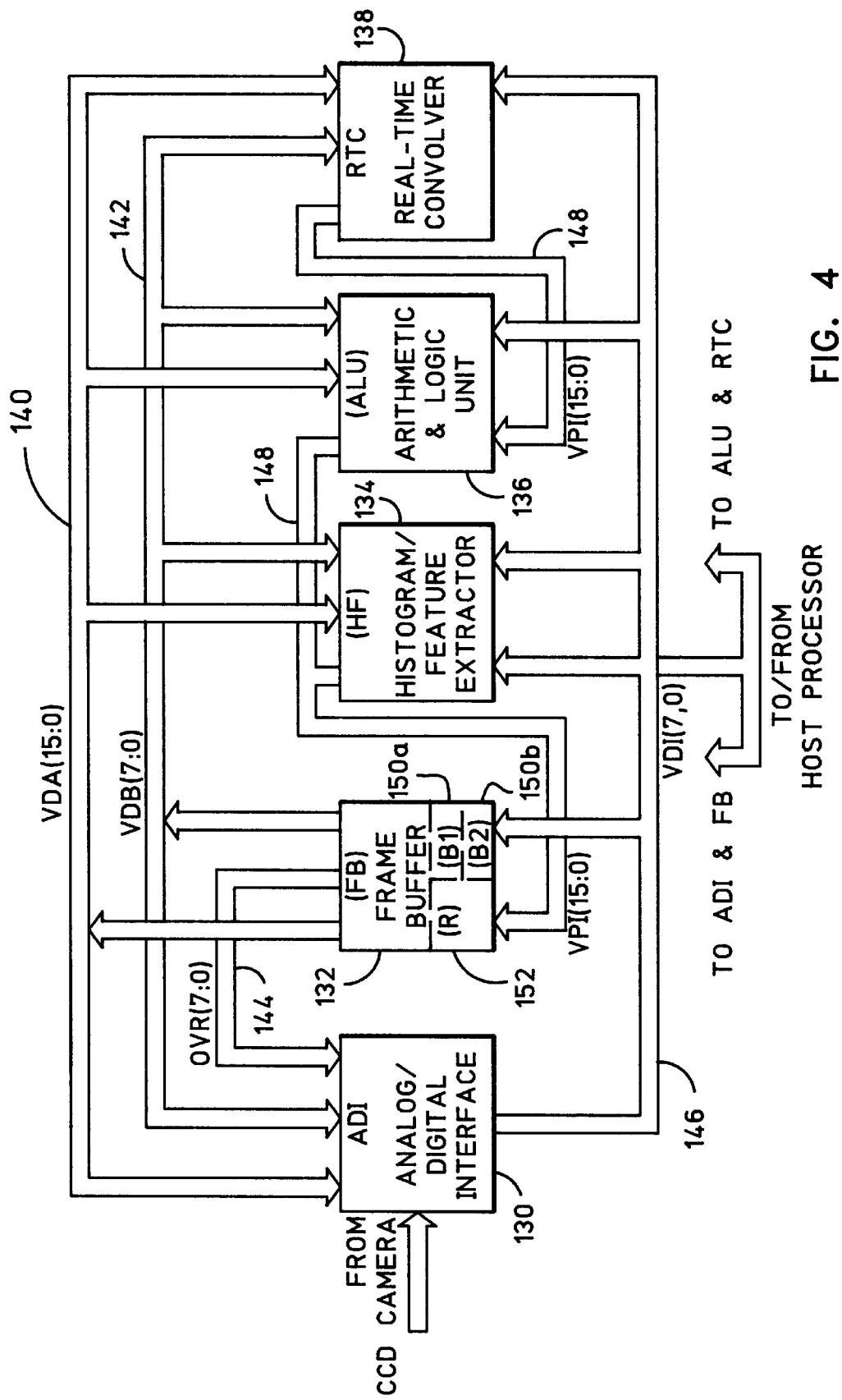
FIG. 4 is a block diagram of the presently preferred image processor of FIG. 1.

A block diagram of the preferred image processor 110 is illustrated in FIG. 4. It should be observed that while an image processor will generally speed up the image segmentation of the present invention, there is no reason why the calculations performed therein could not take place in the host processor 112 (FIG. 1) or any other computer.

The image processor 110 is preferably configured with five functional units, or boards, as follows: (1) an analog/digital interface (ADI) 130, for analog-to-digital conversion of the RS-170 video signal generated by the camera 108 (FIG. 1); (2) a frame buffer (FB) 132, for storage of one 16-bit and two 8-bit 512×512 digital images; (3) the histogram/feature extractor (HF) 134, for creating histogram and feature arrays; (4) an arithmetic & logic unit (ALU) 136, for multiplication, addition, subtraction, logical operations, and bit shifts; and (5) a real time convolver (RTC) 138, for 4×4 or smaller convolutions.

The preferred image processor 110 performs all the above operations in real time (1/30th seconds), or faster in area-of-interest (AOI) mode. AOI mode allows the selective processing of only a portion of a digital image. The time required for AOI mode operations is proportional to the number of pixels, or picture elements, in the selected region.

Understanding the basic mechanisms by which the five image processor boards 130, 132, 134, 136, 138 communicate and function is important for understanding the present invention. Image operations, such as subtraction, multiplication, and convolution are carried out by the ALU 136 and RTC 138. The ALU 136 and RTC 138 are pipeline processors. This means that image information flows into these boards 136, 138, is operated on, and flows out. The image information is always flowing. If the ALU 136 is set up for multiplication of two images stored in the FB 132, then one multiplication is occurring every 33 milliseconds as long as the set-up remains and the image processor 110 is powered on. Control is maintained by having the host processor 112 instruct the FB 132 to acquire the information coming from the processors 130, 136, 138. From the point of view of the FB 132, information flows out over three buses, video data A (VDA) 140, video data B (VDB) 142, and overlay (OVR) 144, and in over two buses, video data in (VDI) 146 and video pipeline in (VPI) 148. The FB 132 is always broadcasting information over its output buses and information is always available to it over its input buses. If the instruction to acquire is not sent to the FB 132, the results of the operations are not stored. Programming the operations of the boards in the Series 151, therefore, is a matter of controlling the flow of image information as well as setting specific operations on or off.

The frame buffer 132 contains 1 Megabyte of random access memory organized as two 8-bit×512×512 image stores called, respectively, B1 150a and B2 150b, and one 16-bit×512×512 image store called A, or FRAMEA, 152.

FRAMEA 152 can also be treated as two 8-bit images. The VDA 140 continuously carries the 16-bit information stored in FRAMEA 152 and the VDB 142 continuously carries 8-bit information stored in either B1 150a or B2 150b. A multiplexer (not shown) controls which image is carried by the VDB 142, i.e., the image stored in B1 150a or B2 150b. Control over which image is operated on is maintained at the input to the pipeline processors 136, 138. The image output from the pipeline processors 136, 138 is available only on the 16-bit VPI 148. This processed VPI image information can be acquired directly only by FRAMEA 152. The 8-bit overlay bus (OVR) 144 is used to create an overlay (for display of nuclei edges on a monitor that is not shown) on the images stored in FRAMEA 152 and B1 150a using information stored in B2 150b.

The analog/digital interface 130, the primary responsibility of which is conversion of the analog video signal (from the CCD camera 108 in FIG. 1) to digital format, also acts as a simple pipeline processor. It has access to the VDA and VDB buses 140, 142 and can perform look-up table transformations on information from these buses and broadcast the transformed images over the VDI 146. The 8-bit VDI image information can be acquired directly by B1 150a or B2 150b, and indirectly by FRAMEA 152 through the pipeline processors 136, 138. The VDI 146 also carries the images acquired from the camera inputs, one of which is used for the CCD camera 108. Image transfer from B1 or B2 150 to FRAMEA 152 must be performed through the ALU 136 (with or without processing) and information from FRAMEA 152 can be transferred to B1 or B2 150 through the ADI 130.

Information can also be transferred from the Series 152 image processor 110 to the host processor 112. In addition to reading image information in the form of pixel intensities, most of the registers (not shown) of the image processor 110 can be read to determine the operations currently set. Processed image information is available from only two sources: the ALU 136 min/max registers and the HF 134. The ALU 136 can determine the minimum and maximum intensities in an image and the HF 134 provides more complicated processing, histogram compilation and feature extraction. The HF 134 provides no pipeline processing. Images read by the HF 134 are converted into information read only by the host processor 112. There are no image output buses carrying images altered by the HF 134.

Real-time histogram and feature extraction capabilities of the image processor 110 (FIG. 1) are important for timely operation of the cytometer 100. The histogram array (not shown), generated by the HF 134 in histogram mode, is an array containing the number of pixels in the image at each intensity (e.g., for an 8-bit pixel, gray-scale image, the intensity range is 0, representing minimum intensity, to 255, representing maximum intensity). The histogram can be used for intensity statistics. For example, obtaining the average and standard deviation in the image for the purpose of autofocus. In feature extraction mode, the HF 134 provides an organized array of all pixels at defined sets of intensities. As will be further discussed below, the groups of pixels or "streaks" are compressed by the HF 134 using the well-known method of run-length encoding (RLE). The Series 151 is programmed by writing to registers on the processing boards. A set of higher level routines is provided by the Series 151 Library.

Figure 5:
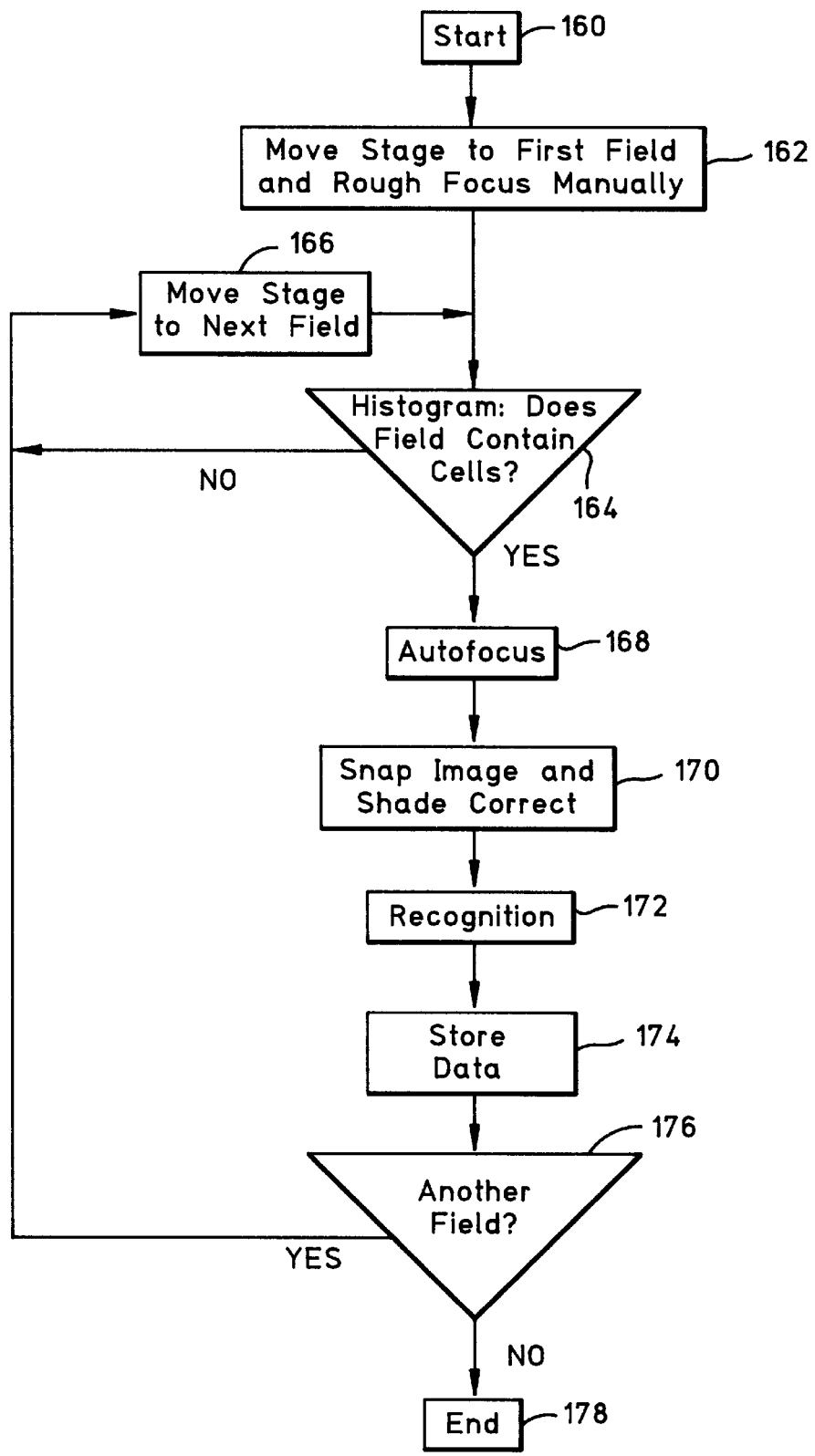
FIG. 5 is a flow diagram of the computer program that controls the image cytometer of FIG. 1.

FIG. 5 illustrates the process for controlling the operator independent cytometer 100 of FIG. 1, beginning at a start state 160. Prior to starting the scanning cytometry program, the scanning area is defined, the shade correction image is calculated (scanning area and shade correction are discussed below), and the gain and offset on the image processor and camera are set. Gain and offset are adjusted with the aid of an oscilloscope to read the analog video signal and a histogram overlay to view the range of image intensities. (The histogram overlay is a graphical plot of pixels number vs. intensity, created from the histogram array provided by the image processor 112. This plot is overlayed on the image displayed on a monitor.) These adjustments are made to set the background to zero intensity and ensure that the intensities fall as much as possible within the measurement range of the system (presently an 8-bit range of 0 to 255).

Software for the preferred image cytometer 100 was written using the Imaging Technology 151 Library, Version 2.3, and the Microsoft C Compiler, Version 5.1. The 151 Library contains routines for basic hardware control of the image processor 110. In order to develop the software detailed in the attached Microfiche Appendix, a library consisting of higher level subroutines was written. Both libraries were used to write a Series 151 interactive command program for subroutine testing prior to incorporation into the image cytometer program, which resides on the host processor 112. Nonetheless, one skilled in the technology will recognize that the steps in the accompanying flow diagrams can be implemented by using a number of different compilers and/or programming languages.

From the start state 160, the cytometer 100 moves to a state 162 to set-up the first field. The scanning area for a 20× objective may, for example, comprise 8,000 fields, or 512× 480 pixel images, that are each approximately 250×330 microns. The motorized stage 103 (FIG. 1) is moved to a first field and the microscope 102 is then focused manually for an initial, rough focus.

Moving to a state 164, the cytometer 100 tests whether the field under consideration contains any cells. Movement to a new field occurs at a state 166 if image intensity is too low to contain a nucleus (or when analysis of one field is complete). For example, if there are less than 801 pixels of intensity greater than 35, autofocus is not performed. This number of pixels is calculated from the image histogram. By definition, adjacent fields do not overlap and nuclei touching the image border are ignored. If an image is bright enough to contain a nucleus, then the cytometer 100 proceeds from the decision state 164 to an autofocus state 168.

Autofocus is a requirement for any fully automated microscope-based image processing system. Autofocus is necessary because of the small depth of field in the microscope 102 (FIG. 1), typically on the order of a micron. It is more practical to perform autofocus on each new field than to achieve the otherwise required flatness over a few square centimeters. For this reason, various autofocus functions were tested to determine those best suited for image cytometry.

Note that autofocus is controlled from the host processor 112 (FIG. 1). The host processor 112 can perform a transformation on the image to obtain a value which represents a degree of focus. This value can then be compared with another value obtained from another image after the stage 103 is moved up or down via the XYZ stage controller 106.

There are several fundamentally different methods in use for autofocus. Most of these methods fall into two categories: position sensing and image content analysis. Position sensing methods, such as interferometry, require independent evaluation of the best focus location and, more importantly, a single well-defined surface from which to reflect light or sound. In biologic specimens there are usually two reflective surfaces, the coverslip and slide. In addition, tissue specimens with significant depth lie on a slide and best focus is not necessarily achieved at the surface of the glass. These problems make absolute position sensing methods impractical for use in light microscopy. Image content analysis functions, on the other hand, depend only on characteristics measured directly from the image.

The cytometer 100 (FIG. 1) of the present invention uses an image content analysis function for autofocusing the microscope 102. Best focus is found by comparison of an image characteristic between a series of images acquired at different vertical positions. This method of autofocus requires no independent reference and, as long as the coverslip is clean, is not affected by the second reflective surface. Its most important limitation is speed, which is dependent on the video rate of the camera 108, the time for repositioning the stage 103, and function calculation time in the image processor 110 and the host processor 112.

Conceptually, autofocus functions are based on the observation that images increase in contrast and image sharpness as focus improves. If an image consists of light and dark regions, the light regions become darker and the dark regions become lighter as the microscope 102 is moved farther from focus. This change in contrast can be described mathematically by the change in variance or standard deviation of pixel intensity, i.e., an increase in contrast corresponds to an increase in standard deviation.

If an image contains discrete objects with well defined edges, the edges blur as the image moves out of focus. Image sharpness can be measured by analyzing the Fourier frequency spectrum of the image, or by the application of gradient filters that isolate higher frequencies in the image. The magnitude of the high frequencies or gradients can then be used as a measure of best focus. Either of these magnitudes, or a combination of thereof, is obtained using a selected autofocus function.

The specimens utilized thus far for the image cytometer 100 consist of a fixed monolayer of cells stained with a fluorescent dye. The next step in complexity is the analysis of live fluorescent-stained cells. Because fluorescent excitation, especially with UV light, is toxic to cells, it is best to limit the exposure as much as possible. With a computer-controlled shutter the exposure can be limited to <66 ms for the acquisition of each image. Autofocus has been found to require the testing of a minimum of about seven positions for reliable focus. If the fluorescent image is used for focusing, eight times more exposure to light is required than for acquisition of a single image. One possible method for reducing the exposure is to perform autofocus using phase contrast microscopy, and subsequently acquire a single fluorescent image for analysis. Therefore, in addition to evaluation of autofocus using fluorescent images, autofocus functions for phase contrast images have also been studied by the present inventors. More details of different approaches for autofocus can be found in the doctoral dissertation of Jeffrey H. Price entitled *Scanning Cytometry for Cell Monolayers*, University of California, San Diego, 1990, which is hereby incorporated by reference.

One presently preferred autofocus function, termed F15 in the incorporated dissertation, has been found satisfactory for the applications of the image cytometer 100 attempted to date. The autofocus function F15 is a combination of the 3×3 Laplacian (a well-understood function for measuring image sharpness) and the variance (a well-understood function for measuring image contrast). An intermediate image was formulated with the convolution kernel as follows:

$$\begin{matrix} -1 & -1 & -1 \\ -1 & 9 & -1 \\ -1 & -1 & -1 \end{matrix} \qquad (1)$$

and the variance was calculated from this image. In the preferred cytometer 100, the convolution kernel is fed to the real-time convolver 138 (FIG. 4) and the variance of the filtered image is calculated by the host processor 112 via the histogram array generated by the HF 134. The sharpening filter (1) is equal to the sum of the 3×3 Laplacian and the original image. The idea behind this function is to combine the effects of gradient functions, which measure edge sharpness using first or second derivatives, with the effects of contrast measurement functions, which utilize the variance or standard deviation of image intensity.

F15 has been used for autofocus over 65,000 times on images of fixed, 4', 6-diamidino-2-phenylindole dihydrochloride (DAPI) stained cells. This function has been observed to be fast and reliable. It was implemented with the convolution results set to 8-bit positive. The algorithm uses the well-known binary search algorithm to move the stage 103 (FIG. 1) and locate best focus. The search range is fixed and the center of the range is the best focus at the previous microscope field. In the preferred cytometer 100, the combination of stage movement to an adjacent field and autofocus requires about 1 second.

After autofocus, the image cytometer 100 proceeds to a state 170 to "snap", or acquire, a new image, i.e., obtain a digital image from the CCD camera 108 via the analog/digital interface 130 (FIG. 4), and shade correct the image. Each time an image is acquired for analysis, it must be shade corrected to compensate for uneven illumination. Shade correction is performed by multiplying the new image with a correction image which is prestored in the host processor 112. The shade correction image is calculated from a flat-field image.

A flat field is preferably created by adding 5 μg/ml DAPI and 1 mg/ml DNA (oligonucleotides from herring sperm, D-3159, Sigma, St. Louis, Mo.) to a buffer solution containing 10 mM TRIS, 10 mM EDTA, 100 mM NaCl, and 1% 2-mercaptoethanol. This homogeneous solution fluoresces evenly, providing an image that would be uniform if the light source and optics were perfect. This solution is placed in a depression machined into an acrylic block and viewed through a coverslip sealed with vacuum grease. To minimize variation due to imperfections in the coverslip, the objective-coverslip distance is made as small as possible and the stage is moved laterally during a 256 frame average.

Shading distortion is corrected by multiplying each pixel in the new image by the ratio of the average flat-field intensity to the flat-field pixel value, as is known in the technology. This operation was performed by the ALU 136 (FIG. 4) using an image calculated from the flat-field image. The ALU bit shifter (not shown) allowed this floating point calculation to be carried out in conjunction with the ALU integer multiplier (not shown). The shade corrected image was calculated by the host processor 112 (FIG. 1) in floating point arithmetic, bit-shifted left by seven bits, rounded and stored. The shade correction was applied by multiplication of this image with each new image. A 7-bit right rotate recovered the truncated result after multiplication and preserved the remainder bits. Preservation of these bits allowed rounding by use of the ALU compare operation and conditional look-up tables. Although about a minute is required for calculation of the shade correction image prior to starting the image cytometer program (FIG. 5), the subsequent shading corrections are each performed in real-time.

In FIG. 5, after shade correction of the digital image, the image cytometer 100 moves to a recognition, or image separation, function 172. Recognition is the conversion of the array of pixels making up a digital image into an accurate, easily accessible representation of the image objects in computer memory.

The simplest way for a computer to identify pixels is by differences in intensity, i.e., in a continuous tone or gray-scale image. DAPI stained cells (further discussed below) create images of high contrast, facilitating recognition. Even with this high contrast, however, it is not possible to accurately recognize all nuclei by a single intensity range. This is due to the fact that the edges in images often exhibit a gradual, rather than abrupt change in intensity from object to background. The immediate background of brighter nuclei is often equal to or greater than the intensity of dimmer nuclei. If the threshold is low enough to include the dimmest nuclei, the selection of the brightest ones contains a significant number of background pixels, or image points.

This problem is overcome by two methods: digital filtering and object intensity dependent thresholding. The three main steps of the recognition function 172 of the present invention are: 1) application of a digital filter, such as convolution, Fourier, etc., to the image thus creating an intermediate feature extraction image, 2) first selection of each nucleus with a single threshold, and 3) reselection, or second selection, of each nucleus using a local threshold calculated from average intensity of the nucleus found in the first selection. These steps will be further discussed below with reference to FIG. 6.

After the recognition, or image segmentation, of a field, the image cytometer 100 continues to a state 174 to store the object data on the hard disk (not shown) of the host processor 112. If, at the subsequent decision state 176, it is determined that more fields of the specimen 114 (FIG. 1) need to be processed, then the image cytometer program proceeds to state 166 to begin another cycle with a new field. Otherwise, if all fields have been processed, the program terminates at an end state 178.

Figure 6:
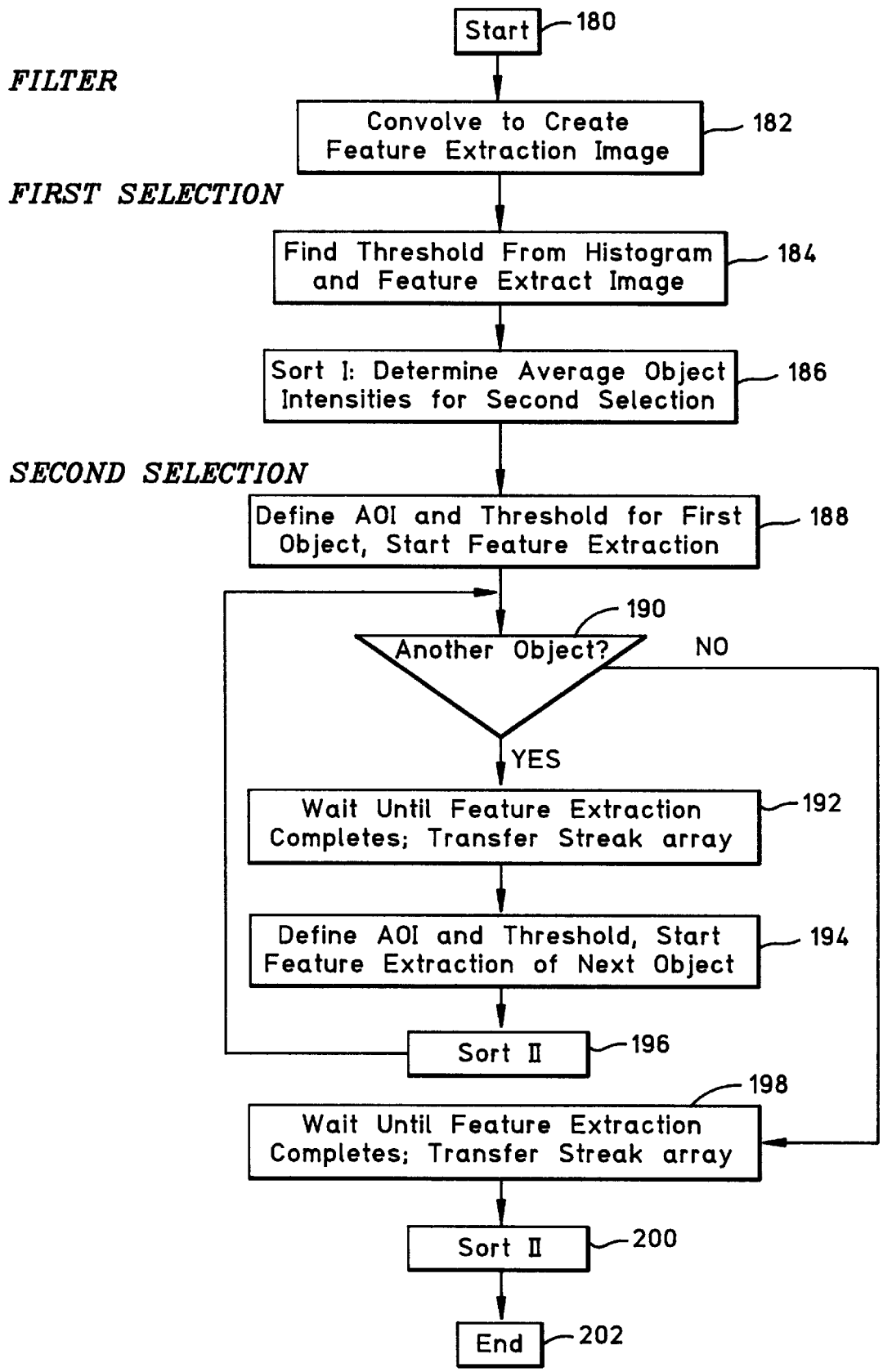
FIG. 6 is a flow diagram of the image separation portion of the flow diagram shown in FIG. 5.

The image segmentation method of the present invention is illustrated by the flow diagram of FIG. 6. The image segmentation function 172 is a part of the image cytometer process as shown in FIG. 5. The filter, the first selection, and the second selection, form a method for finding object pixels in the image.

In FIG. 6, the image segmentation function 172 (FIG. 5) begins at a start state 180 and proceeds to filter the image at a state 182. The edge is the most difficult part of the object to select accurately. Edge pixels may be thought of as either the maxima of the first derivative or the zeros of the second derivative (non-saddle inflection points) of intensity with respect to X and Y. The purpose of the filter is to increase the edge gradient. The larger edge gradients in the filtered image result in feature extraction more insensitive to threshold selection that follows filtering.

Presently, a convolution filter is used to filter the image. The convolution filter, or kernel, is loaded by the host processor 112 (FIG. 1) into the real-time convolver (RTC) 138 (FIG. 4). The convolution is well-understood and may be concisely defined as follows:

$$u_{i,j} = c * g_{i,j} \qquad (2)$$

where:

$u_{i,j}$ is the pixel at the ith row and jth column of the filtered image;

c is the convolution filter;

$g_{i,j}$ is the pixel at the ith row and jth column of the original digital image; and

* is the convolution operator.

In the presently preferred embodiment, the convolution filter is a 4×4 kernel. The size of the kernel is limited by the presently preferred image processor 110. However, it is expected that larger kernels may provide a better degree of filtering.

The preferred convolution kernel that is used to enhance the contrast and increase the edge gradient is as follows:

$$\begin{array}{rrrr} -2 & -1 & 1 & -2 \\ 1 & 3 & 3 & -1 \\ -1 & 3 & 3 & 1 \\ -2 & 1 & -1 & -2 \end{array} \qquad (3)$$

The convolution that uses the above kernel is the equivalent of the following equation:

$$\begin{aligned} u_{i,j} = &-2g_{i-2,j-2} - g_{i-2,j-1} + g_{i-2,j} - 2g_{i-2,j+1} + \\ & g_{i-1,j-2} + 3g_{i-1,j-1} + 3g_{i-1,j} - g_{i-1,j+1} - g_{i,j-2} + 3g_{i,j-1} + \\ & 3g_{i,j} + g_{i,j+1} - 2g_{i+1,j-2} + g_{i+1,j-1} - g_{i+1,j} - 2g_{i+1,j+1} \end{aligned} \qquad (4)$$

where:

$u_{i,j}$ is the pixel at the ith row and jth column of the filtered image; and $g_{i,j}$ is the pixel at the ith row and jth column of the original digital image.

The result of the convolution is divided by 2 in the RTC 138 (bit shift right one). If a pixel is >255 the ALU 136 sets it to 255 and if it is <0 it is set to 0. This kernel averages the images on a 2×2 scale (the 3s in the kernel) and sharpens them on 4×4 scale (the negative numbers in the outer positions). The positive 1s in the outer positions also increase the averaging effect. Convolution with this kernel and the subsequent bit shift would cause an image of a single, nonzero intensity to double in brightness. This effect increases the contrast in images with multiple intensities.

The filtered image facilitates the use of a relatively simple threshold selection method. The gradient, however, is not great enough to select all nuclei with the same threshold. A second selection, using an improved threshold, is required. The sharpening effect of the filter and the second threshold selection are next demonstrated on the sample nucleus shown in FIG. 3.

Figure 7:
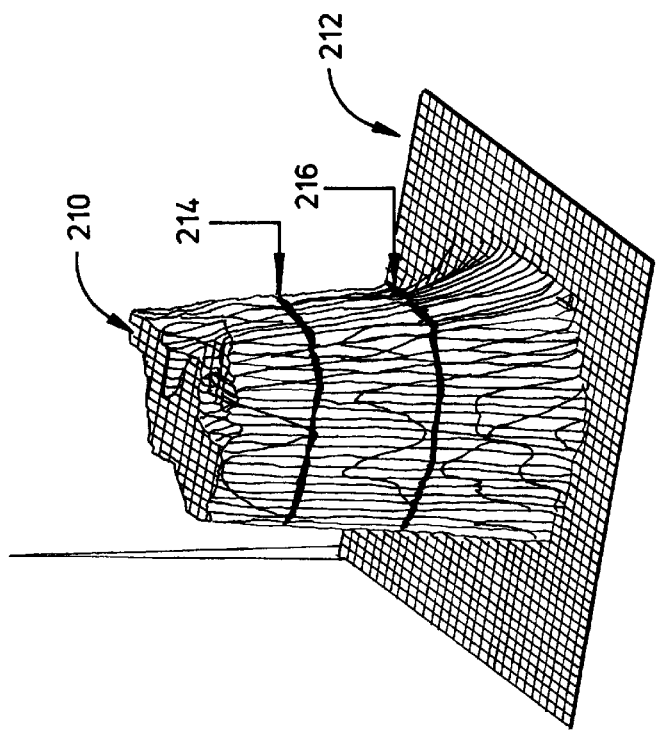
FIG. 7 is a three-dimensional plot of the object shown in FIG. 3, after convolution filtering.
Figure 8:
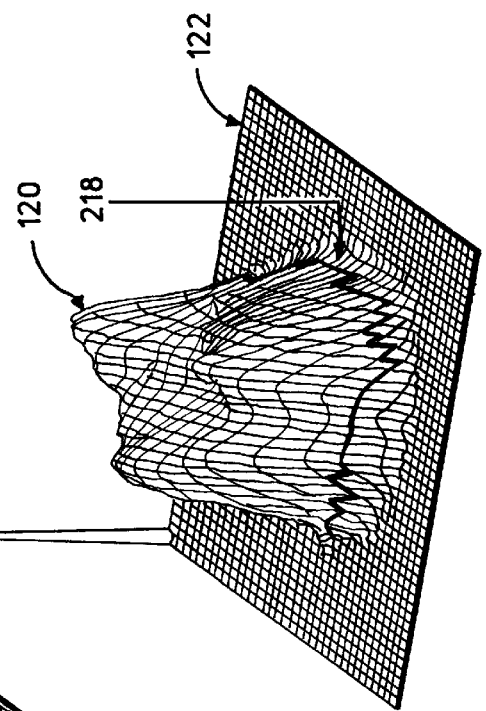
FIG. 8 is a three-dimensional plot of the object shown in FIG. 3, after image separation.

FIG. 7 is the three-dimensional plot of the convolved digital image of a DAPI stained nucleus and FIG. 8 shows the image separation applied to the object 120. The original, shade-corrected image (e.g., FIG. 3) is used to compile final intensity parameters as the features from the convolved image are sorted the second time (states 196, 200). Intensity parameters for calculating the second threshold are compiled from the filtered image during the first sort 186. All nuclei are first selected using a single threshold (not shown). The estimated average intensity of each convolved nucleus is then calculated and used to find an improved threshold. In FIG. 7, the estimated average intensity of 190, indicated at 214, and the threshold of 100, indicated at 216, are overlayed on the plot of the example convolved object 210. In FIG. 8, an overlay 218 on the original object 120 shows the final selection of the nucleus resulting from this threshold; all pixels inside the overlay 218 are part of the nucleus.

Referring to FIG. 6, after filtering the image at state 182, the system moves to a state 184 wherein the first threshold is obtained by finding the first maximum in the histogram, obtained from the histogram/feature extractor 134 (FIG. 4), and adding a constant. Proceeding to state 186, the thresholds for the second selection are calculated by subtracting a constant from the average intensity calculated for each object in the first selection. The lower limit for the second threshold is two-thirds of the first threshold.

By way of an overview, object selection is accomplished by extracting the feature pixels into an array and sorting the array onto a data structure (Sort I). At state 188, given the intensities defining the feature pixels, the histogram/feature extractor 134 (FIG. 4) of the image processor 110 performs feature extraction by returning a streak array, at state 192, which contains all positions of the corresponding pixels in a compressed form. Each time this occurs, i.e., another object is found at state 190, the array must be sorted by the host processor 112 to select individual objects.

Moving from state 192 to state 194, the second feature extraction is performed in area-of-interest (AOI) mode on the image processor 110, which is significantly faster than normal mode. An AOI window is chosen by adding a border around the circumscribed rectangle, defined for each object in the first selection by its minimum and maximum x and y pixel positions. Each nucleus is isolated from its neighbors by ignoring objects touching the AOI border and comparing the remaining objects to the original. To further speed execution, continuing to state 194, the second sort, Sort II, is carried out in parallel by initiating feature extraction of the next AOI before beginning the sort.

After each feature extraction, the pixel locations are sorted by the host processor 112 onto a data structure (not shown) representing the objects as shown in FIG. 6 at the states 196, 200, which both refer to the Sort II function. (The state 198 performs the same function as state 192, discussed above.) Sort II is further discussed with reference to FIG. 9. After all objects have been separated from the image, the image segmentation function terminates at an end state 246.

Figure 9:
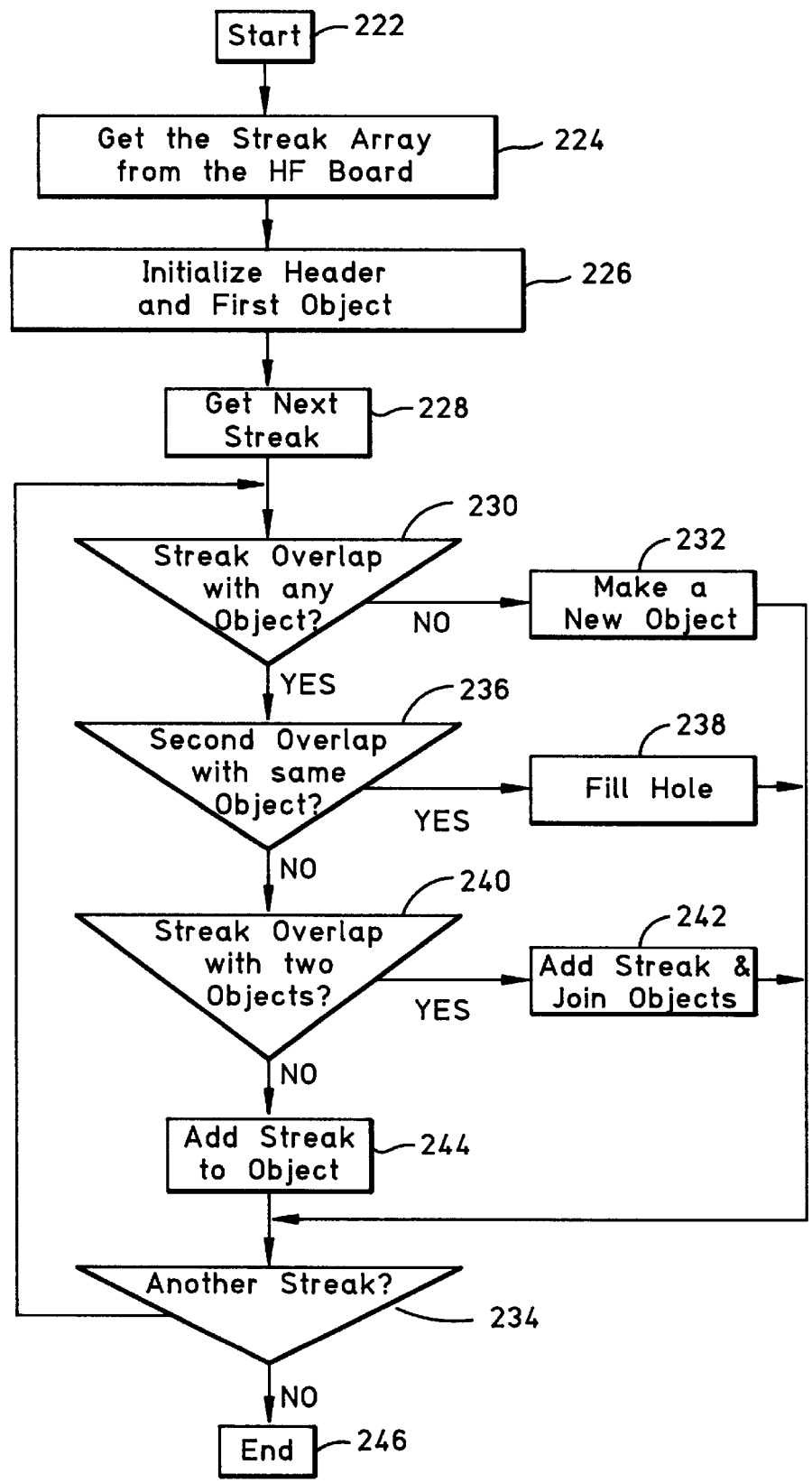
FIG. 9 is a flow diagram of the Sort II portion of the flow diagram shown in FIG. 6.

FIG. 9 illustrates the control flow for the Sort II function (a portion of the image segmentation function shown in FIG. 6) that sorts image features, or streaks, into objects beginning at a start state 222. The flow diagram of FIG. 9 is the functional equivalent of the source code for Sort II, which is included in the attached Microfiche Appendix. It should be observed that Sort II essentially incorporates the Sort I state 186 (FIG. 6) used in the first selection step of the image segmentation function; however, Sort I does not include the hole filling step as defined in Sort II.

The Sort II function operates on an object data structure, stored in the RAM memory of the host processor 112 (FIG. 1), that relates individual streaks (from the image processor 110) into objects. The data structure, called the object list, is a circular, doubly-linked list of object structures, each pointing to a doubly-linked stack of the lines defining the spatial extent of the object. Moving to a state 224, the first pixel position data are provided in the form of a streak array by the HF 134 (FIG. 4). A streak consists of the three values, x and y start location and the length (1), denoting a horizontal set of contiguous feature pixels. This form of data compression has also been called "run length encoding" or "chord encoding".

Next, the object list is initialized at a state 226 by placing the first streak into a first object structure. A line structure consists of the x, y, and l of one streak and pointers to the next and last lines on the stack. Each object structure contains descriptive information, pointers to the next and last objects in the list, and a pointer to the line stack. The descriptive information includes the minimum and maximum x and y values, object number, integrated intensity, area, and the sum of the squares and standard deviation of the pixel intensity. These variables, with the exception of the standard deviation, are calculated as the streaks are sorted. The sum of the squares is used to calculate the standard deviation after the sort is completed.

Now, subsequent streaks are obtained from the HF 134 at a state 228. At the decision state 230, it is determined whether the new streak overlaps any object already contained in the object list. The Sort II function groups all connected streaks into the same object. Two streaks belong to the same object if any pixel from the first is eight-connected to any pixel from the second. With this definition, two feature pixels are connected if the first is one of the eight nearest neighbors of the second. Let one streak be x1, y1, l1 and the other be x2, y2, l2. These two streaks are connected if $|y1-y2|=1$, i.e., the streaks are in adjacent rows, and if the following condition is satisfied:

$$(x1<=x2+l2) \text{ and } (x2<=x1+l1) \tag{5}$$

Equation (5) mathematically describes the notion of columnar overlap between streaks. Thus, if at the decision state 230, it is determined that the new streak does not overlap any other streak in the object list, then the Sort II function creates a new object structure and links it into the object list, as shown in FIG. 9 at state 232. The function then proceeds to a state 234 to determine whether another streak is available from the HF 134.

Now, returning in the discussion to state 230, if overlapping streaks are found, the function continues to a decision state 236, wherein a test is made as to whether the new streak overlaps two streaks in the same object.

Most nuclei contain considerable detail and create images with internal intensity variations and edges. The sharpening filter accentuates this detail, sometimes causing areas within the nucleus to fall below the threshold. This results in holes in the feature data representing the nucleus. These holes are filled during the second sort after moving from the state 236 to a state 238.

Filling the holes requires searching in both directions on the line stacks and is the reason for making them doubly linked. A hole is encountered when the streak being sorted is connected to more than one line in the same object. The pair of line structures to which it connects also define the entry point for the hole filling routine. The holes are filled by finding all connected hole streaks and combining the pairs of line structures defining each. The set of contiguous pixels between two line structures of the same y value define a hole streak if they are connected to the entry hole streak.

Two hole streaks are connected if any pixel from the first is four-connected to any pixel from the second. Two pixels are four-connected if the first is one of the four nearest neighbors of the second. This definition differs from eight-connected by excluding the four closest diagonal pixels. The search for all connected hole streaks uses a stack, consisting of pointers to the first of the pair of line structures defining each one. The entry hole streak is placed on the stack and the search is begun. A hole streak is removed from the stack and closed. Then all line structure pairs with y positions one less and one greater are checked and added to the stack if they define a hole streak. The cycle repeats until the stack is empty and the hole is filled. Once the hole is filled, the function proceeds to decision state 234.

Otherwise, if at the state 236 it is decided that the new streak does not overlap a second streak in the overlapping object, the Sort II function moves to a decision state 240 to query whether the new streak overlaps another object. If a streak connects with lines from two objects, they are joined at a state 242. The streak array is ordered left to right and then top to bottom, with the x-y origin at the upper left corner of the image. This order is utilized to speed sorting by maintaining object list order in increasing x and dividing the list into active and inactive parts. An object becomes inactive when its greatest y is two or more less than the streak being sorted. Only the line stacks of active objects with appropriate x extrema are checked for connectivity. After adding the streak and joining the objects in the object list, Sort II moves to the decision state 234 as discussed previously.

From the decision state 240, if it is determined that the new streak does not overlap with two objects, the Sort II function proceeds to a state 244 to add the streak to the overlapping object, and then moves to decision state 234. The cycle of processing a new streak then continues to the state 228, if one exists. Otherwise, the Sort II function terminates at an end state 246.

Applications of the Image Cytometer

The device of the present invention makes fully automated, operator-independent image cytometry practical for use with attached cells. The scanning cytometer recognizes and measures parameters of labeled (e.g., fluorescent-stained) cell features of attached cells. The device locates each cell in each image and computes quantitative information about the amount of labeled cellular substance and its shape and distribution. For example, the DNA content and distribution, and nuclear shape parameters, can now be identified and recorded with the device of the present invention. The device and methods described herein, which are used, for example, to measure DNA content and cell nucleus parameters, are equally applicable to other cell features and components.

The present invention is not limited to use in scanning DNA or nuclear material. Other applications include, without limitation, ploidy analysis of cells; analysis of cellular components including organelles and plastids; analysis of specific cell-derived molecules, such as macromolecules; and improved analysis of cells or other materials, whether biological, organic or inorganic, by the presently-disclosed image analysis techniques.

In addition, accurate recognition of the cell feature in the image is an important step in achieving a fully automated operation. Others have used simple intensity thresholding (which correctly recognizes, at best, about 85% of the cells analyzed) or mathematical morphology (recognition rate unknown; see, e.g., C. J. Moran, *A Morphological Transformation for Sharpenina Edges of Features before Segmentation*, Computer Vision, Graphics, and Image Processing, Vol. 49, pp. 85–94, 1990) for image segmentation and recognition. The presently-disclosed method, which yields a much higher accuracy recognition rate, is summarized as follows:

ACQUIRE IMAGE→FILTER→THRESHOLD

More detailed discussion of this method is provided herein. Also, the selection is refined by a second threshold for each individual object—for example, each individual nucleus.

EXAMPLE I

Cytometry of Attached Cells

The presently-disclosed device and method are preferably used to analyze fluorescent-stained cell features. Other investigators have had limited success with semi-automated DNA content from Feulgen-stained cells; further, none have presented DNA content data from more than 2,500 stained cells, and typically, much less. There are many available fluorescent dyes that stain other cellular features, but very few densitometric stains, such as Feulgen, can be used to quantitate cellular substances. Finally, the methods utilized for densitometric image cytometry do not necessarily apply to fluorescence image cytometry.

While the preferred embodiment utilizes the fluorescent stain DAPI, it should be appreciated by those skilled in the art that other stains or labeling means may be effectively utilized, such as antibodies tagged with fluorescent or chemiluminescent moieties. Examples of fluorescent stains that may be used with live cells include DAPI and Hoechst (albeit the latter is somewhat more toxic than DAPI). U.S. Pat. Nos. 4,906,561 and 4,668,618 discuss the use of DAPI and are incorporated herein by reference. Thioflavin T and thiazole orange are fluorescent stains described in U.S. Pat. No. 4,957,870, which is incorporated herein by reference. Xanthene dyes are disclosed in U.S. Pat. No. 4,933,471, while fluorescently-tagged antibodies are discussed in U.S. Pat. No. 4,983,359; these patents are also incorporated herein by reference. Other fluorescent stains and methods of using same are described in U.S. Pat. Nos. 4,959,301 and 4,987,086, which are incorporated herein by reference. Examples of other fluorescent stains may be found in the current catalog from Molecular Probes of Eugene, Oreg.

The disclosed invention could also be adapted for use with DNA-specific, densitometric, or other stains such as Feulgen Azure A, chromogen, methyl green, immunohistochemical stains, or ionic stains, for example, albeit they are much less preferred, as fluorescent labels provide advantages over the use of non-fluorescent ones. (See, e.g., U.S. Pat. Nos. 4,998,284 and 5,016,283, which discuss alternative staining means.)

A. Cell Culture and Specimen Preparation

Cells were prepared for analysis as follows. Normal neonatal foreskin fibroblasts were plated on washed, autoclaved microscope slides. (The cells were obtained form Dr. Robert Hoffman and Dr. Gilbert Jones, Univ. of California, San Diego.) The cells were maintained in Eagle's minimal essential medium with Earle's salts (Irvine Scientific, Irvine, Calif.), supplemented with 10% fetal bovine serum, 100 $\mu$g/ml gentamicin, and 0.26 mg/ml L-glutamine (final concentrations), in a humidified 5% $CO_2$ incubator at 37° C. When the cells reached about 50% confluence the slides were washed in physiologic buffered saline (PBS), fixed for one hour in 4% paraformaldehyde in PBS pH 7.2–7.4, and stained for one hour in DAPI solution. The staining solution consisted of 50 ng/ml 4', 6-diamidino-2-phenylindole dihydrochloride (DAPI), 10 mM TRIS, 10 mM EDTA, 100 mM NaCl, and 1% 2-mercaptoethanol. (See S. Hamada and S. Fujita, *Histochem.* 79: 219–226, 1983, which is incorporated herein by reference.) After staining, the slides were removed, covered with a few drops of the DAPI solution, and sealed with 22×50 mm coverslips and nail polish. This creates a preparation with an excess of staining solution sealed in with the cells, which contributes to stable fluorescence and recovery after photobleaching. The P5 cell line used for demonstration in FIG. 3 (and Figures based thereon, i.e., FIGS. 7 and 8) was prepared the same way. (The P5 cell line is a culture of SV40-transformed skin fibroblasts that are murine in origin, obtained from Dr. Robert Hoffman of the University of California, San Diego, Calif.) This cell line preparation was useful for months, with its experimental longevity being largely dependent upon the quality of the seal between the coverslip and the slide.

B. DNA Content Results

Figure 10:
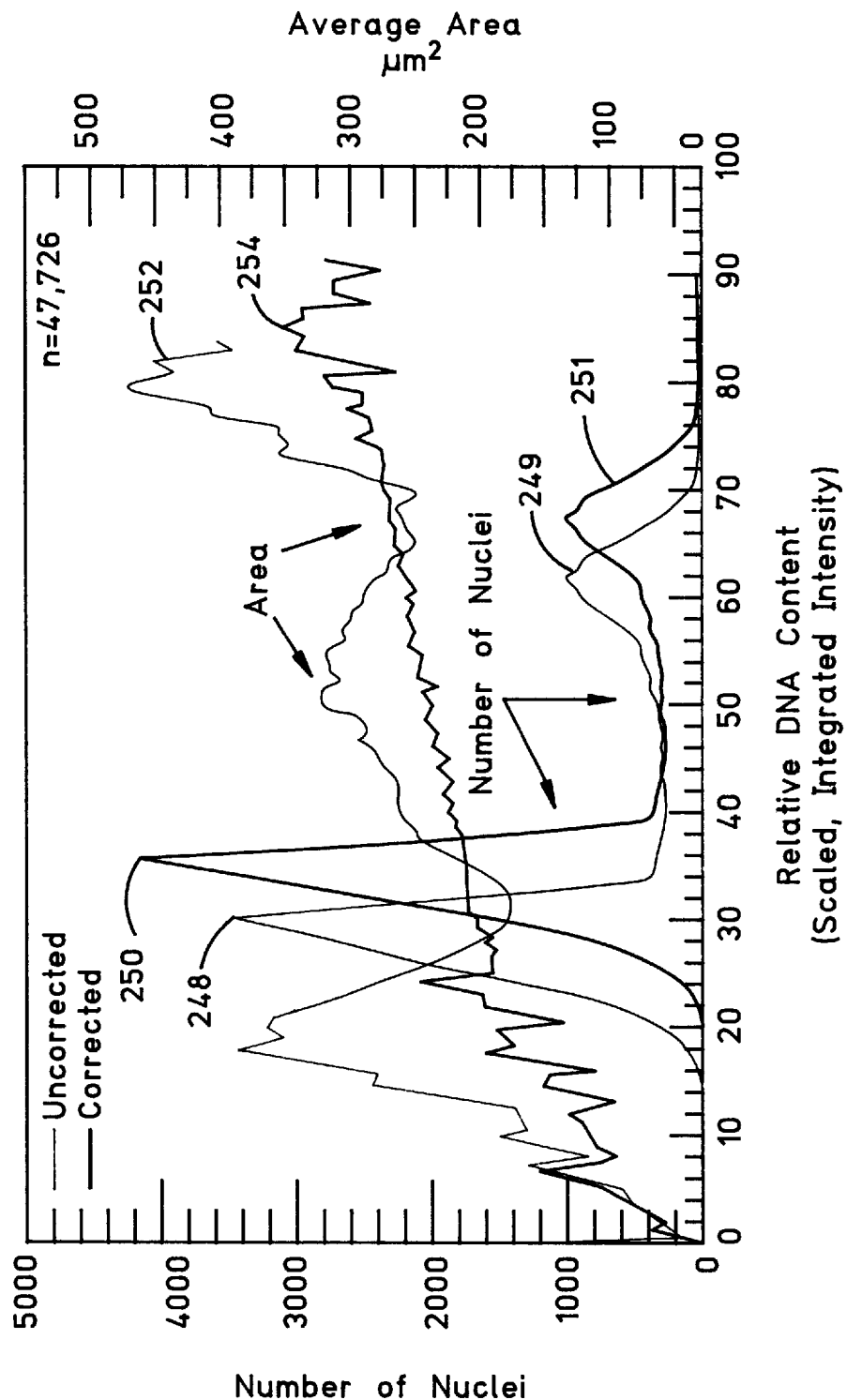
FIG. 10 is a DNA content histogram and average area plot illustrating corrected and uncorrected data from image cytometry.

The results shown in FIG. 10 are an example of the data that can be recorded with this scanning cytometer. FIG. 10 illustrates the results of a DAPI toxicity assay; growth curves for six different concentrations of DAPI, and one control, are shown. These data were obtained in seven hours from 47,726 cells in a 22 mm×50 mm area by analyzing 8,062 images. Relative DNA content, which is proportional to the integrated intensity, is shown on the horizontal axis. The number of nuclei and the average projected area of those nuclei are shown on the vertical axes. Two sets of plots, corresponding to uncorrected (plain) 248, 252 and corrected (bold) 250, 254 data, are shown. The uncorrected and corrected DNA histograms each exhibit two distinct peaks. The peaks on the left 248, 250 correspond to the image objects containing a basal DNA content. The smaller peaks on the right 249, 251 correspond to the objects containing double the basal DNA content. These peaks are referred to as the 2n and 4n peaks, where n is the number of chromosomes and a normal cell contains a pair of each chromosome. Cells about to divide contain twice the DNA content of resting cells. This relationship is exhibited in the corrected histogram, in which the 2n peak is centered at a relative DNA content of approximately 33 and the 4n peak at approximately 66. The cells between the two peaks are in S phase, synthesizing DNA. To create the DNA content data, the integrated intensity of each nucleus was divided by a scaling constant and the result rounded. The number of nuclei at each integer intensity was then summed to create the histogram.

The DNA content histogram is, arguably, subjectively similar to the data acquired with flow cytometry. The flow cytometer uses a single sensor, usually a photomultiplier tube, to measure the fluorescent intensity of cells. The advantage of the photomultiplier tube is increased dynamic range. The disadvantage is limited morphometry. While it can perform some morphometry based on scatter to forward- and side-mounted sensors, it does not have the hundreds of sensors used for each nucleus in the data acquired here. This is an example of the kind of morphometric data that are more difficult to obtain with a flow cytometer because of its low spatial resolution.

Another difference between these two techniques is the fact that the scanning cytometry data contains mitotic cells in both the 2n and 4n peaks, whereas only the 4n peak contains mitotic figures in flow cytometry data. In flow cytometry, the 2n peak is usually referred to as the $G_1$ or $G_0/G_1$ peak, signifying cells in the resting phase of the cell division cycle ($G_1$) or not in the division cycle at all ($G_0$). The 4n peak is called the $G_2$+M peak in flow cytometry, signifying cells that have completely duplicated their DNA or are in mitosis. The 4n or $G_2$+M peak contains all the mitotic cells, because at the early stages of DNA separation, the spatial discrimination of flow cytometry is not great enough to distinguish the two sets of DNA in the same cell. In scanning cytometry, however, as soon as the DNA separates during anaphase of mitosis, the computer "sees" two separate entities each with the 2n DNA content. Because the scanning cytometer in this example recognizes only the DNA, and not the cell, it does not distinguish whether two groups of chromosomes are in the same cell or different cells.

Comparison of the coefficients of variation of the 2n peaks is commonly used to evaluate relative system performance for DNA content measurements. Use of the coefficient of variation is based on the assumption that all cells in 2n contain the same amount of DNA. Although the width of the 2n peak can be affected by cell type, specimen preparation and staining methods, it provides an estimate of the fluorometric precision. The coefficient of variation of the 2n peak in the corrected data is 7.6%. The coefficients of variation reported by the investigators who used simple intensity thresholding for recognition ranged from 11.5% to 12.7%. (See, e.g., T. Takamatsu, et al., *Acta Histochem. Cytochem.* 19: 61–71, 1986.) This is consistent with the coefficients of variation generally associated with image cytometry. (See, e.g., G. L. Wied, et al., *Human Pathology* 20: 549–571, 1989.) The analogous coefficients of variation from flow cytometry range from 2% to 8%. Clearly, then, the precision of the DNA content histogram presented here represents a significant improvement for image cytometry.

C. Discrimination of the Mitotic Figures by Area

Figure 11:
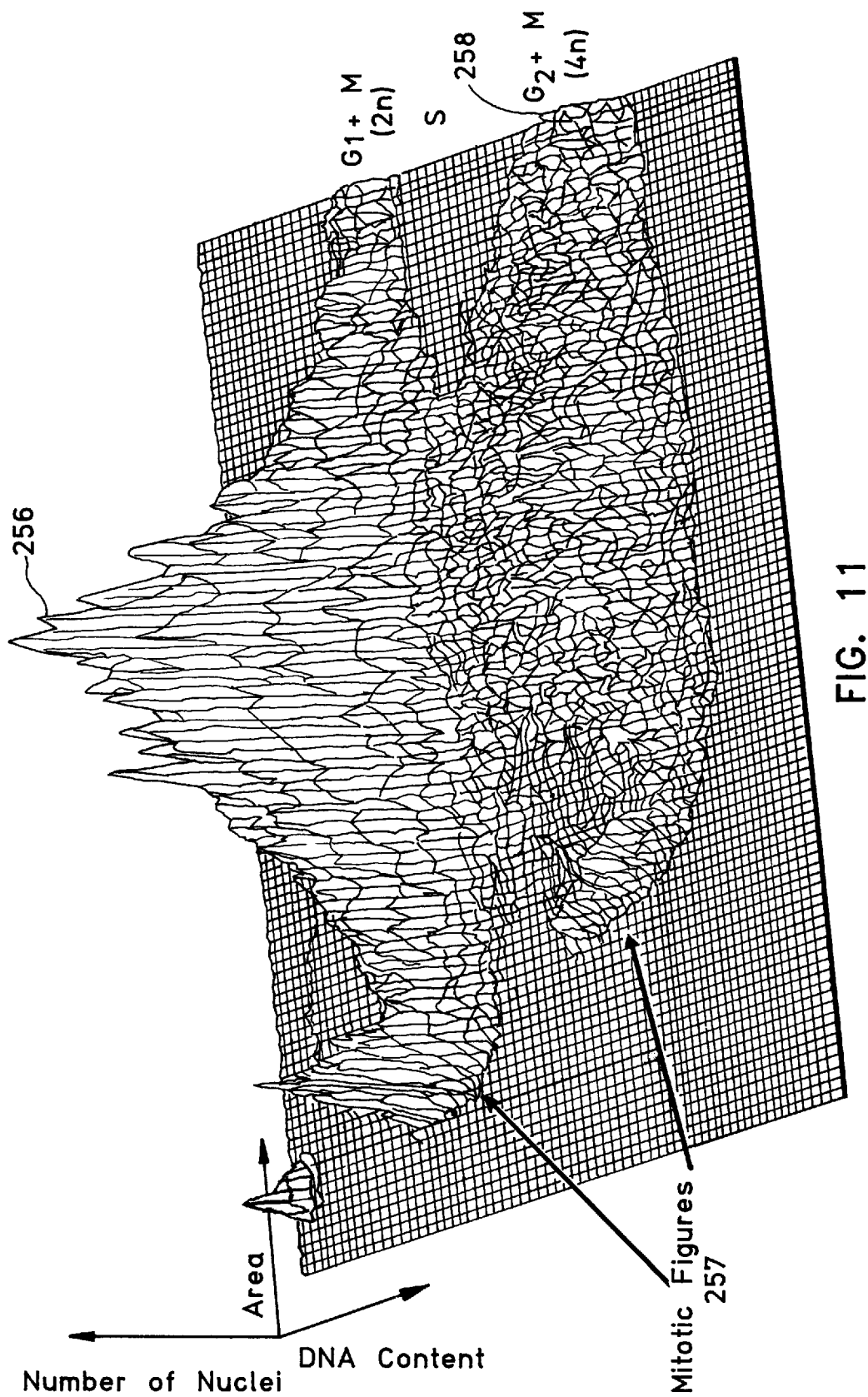
FIG. 11 is a three-dimensional plot illustrating the number of nuclei, the nuclear area, and the DNA content of a cell culture.

Mitotic figures in DAPI stained cell monolayers are easily identified under the microscope by looking for highly condensed, brightly fluorescing nuclei. The fact that mitotic nuclei are so easily identified by the human observer raises the question of how easily they might be automatically identified by computer. FIG. 11 shows a 3D histogram of data produced according to the present invention, specifically, the number of nuclei vs. their area and DNA content. The 2n peaks 256 and the 4n peaks 258 are visibly separated from each other from top to bottom in the figure. The S-phase nuclei are also visible in the valley between (as indicated by reference letter "S" on the right-hand side of the histogram). On the left side, two distinctly separate peaks 257 can be seen. These peaks are likely to represent the mitotic figures. Those objects in the 2n mitotic peak each represent one-half of a mitotic figure. The fact that these are visible as separate peaks raises the possibility of applying a curve fit to the data and automatically locating the mitotic figures.

Note that both mitotic figure peaks 257 are spread out in the direction of DNA content. The mitotic figures 257 should contain either the 2n or 4n DNA content. This spreading of the doubled DNA content mitotic figures into S and the single DNA content mitotic figures into the region representing less than the 2n DNA content is likely an artifact. This example of photometric error, explained further below, is due to the fact that digitization to 8 bits is not adequate to measure the range of intensities present in these preparations. The brightest nuclei are brighter than the maximum intensity that can be measured by the camera at its settings for this experiment. This explanation for the spreading of the mitotic peaks is further substantiated by area vs. DNA content relationship exhibited within each. As the area decreases the measured DNA content, or integrated intensity, also decreases. This is as expected for a photometric clipping error. The more condensed the nucleus, the brighter its average intensity, and the greater the amount of light above the maximum that can be measured by the system. With elimination of this error, the mitotic peaks become taller and more distinct, improving the likelihood of automatic identification.

EXAMPLE II

Cytometry of Live Cells, and Toxicity Studies

Development of scanning cytometry of growing cell monolayers requires attention to cell culture chamber design, the effects of the measurement system itself on cell growth, and the reliability of identifying each cell from scan to scan. The cell culture chamber must provide both an optimal environment for growth and high grade optical accessibility for imaging. The fluorescent dye and excitation light used to create the image must not appreciably affect cell growth. And finally, the interval between scans must be short enough to unambiguously identify each migrating cell, and its daughters after division, for the duration of the experiment.

The cell culture chamber must allow maintenance of temperature, pH, osmolarity, nutrient concentration, and sterility. (See N. M. McKenna and Y. -L. Wang, "Culturing Cells on the Microscope Stage," in *Fluorescence Microscopy of Living Cells in Culture, Part A, Methods in Cell Biology*, vol. 29, Y. -L. Wang and D. Lansing Taylor eds., Academic Press, San Diego, 1989 (see esp. p.108), which is incorporated herein by reference.) Temperature is controlled either by immersion of a sensor in the medium or placement just outside the chamber, while pH is controlled by either gas or chemical buffering. Chambers with medium exposed to gas usually utilize $CO_2$ buffering while those without gas exposure use a chemical buffer such as HEPES. Osmolarity control and nutrient supply are maintained by medium changes. Sterility must be maintained during the transfer of cells to the chamber and while the chamber remains on the stage. Sterility is easiest to achieve if a minimum of chamber manipulation is required after autoclaving and during introduction of the cells.

The presently preferred image cytometer 100 (FIG. 1) utilizes an upright microscope and short working distance objectives for optimal optical quality. Short working distance objectives may require the use of a relatively thin chamber. The problems of humidity control and condensation on the microscope objectives can be avoided by use of a closed, HEPES buffered, continuously perfused chamber. The chamber design thus consists of a glass slide and coverslip of equal rectangular dimensions held 250 $\mu$m apart by a retainer made of teflon. This retainer may contain access ports for the input and output of medium and the placement of a thermistor type temperature probe. Upper and lower aluminum rectangular frames hold the glass pieces in the teflon retainer with enough pressure to create a seal. A thin film of vacuum grease may be applied between the teflon and glass pieces if necessary. All medium infusion will be through the teflon retainer and will contact only the glass once inside the chamber to avoid metallic ion toxicity. Temperature is controlled by use of a probe in direct contact with the culture medium and a heating element in the base plate of the stage. The design allows for assembly prior to autoclaving to minimize the kind of handling that compromises sterility. Cells are introduced by infusion and infusion is stopped long enough for cell attachment. This design will simplify handling and facilitate multi-day microscope stage culturing.

Scanning cytometry is dependent on the use of a fluorescent dye to create images simple enough for computer analysis. To determine the potential for scanning cytometry of live cells, toxicity assays were performed with DAPI on normal human foreskin fibroblasts and a transformed 3T3 cell line. (Useful 3T3 cell lines are readily available; for example, one such cell line is the 3T3 (A31) cell line, ATCC No. CRL 6588, available from the American Type Cell Culture, Rockville, Md.) DAPI stains the DNA of live, as well as fixed, cells. Although the staining is slightly less intense with live cells, it is sufficient for analysis by scanning cytometry. The purpose of the assays was to determine the concentrations at which DAPI begins to affect the growth rate of cells. The definition of toxicity used here includes metabolic changes that might alter the grow rate of cells and is not limited requirement of cell death. The purpose of this definition is to include any effect that the fluorescent dye could have on the parameters that might be measured by scanning cytometry. Ideally, the instrument should not cause any changes in the object it is measuring.

A growth rate assay, utilizing the Coulter counter, was performed on the foreskin fibroblasts. This assay was carried out by plating cells on 7 groups of P-150 culture plates (Nunclon #1-68381, 150×20, available from Myriad Industries, San Diego, Calif.). These consisted of a control group with no dye and 6 groups at concentrations of 10 ng/ml, 50 ng/ml, 100 ng/ml, 500 ng/ml, 1,000 ng/ml, and 10,000 ng/ml of DAPI. Prior to starting the cultures, these concentrations were added to aliquots of a common batch of Eagle's minimal essential medium with Earle's salts, supplemented with 10% fetal bovine serum, 100 $\mu$g/ml gentamicin, and 0.26 mg/ml L-glutamine (final concentrations). Each group consisted of four replicate plates for a total of 140 and the assay was begun by plating 3000 cells on each.

Figure 12:
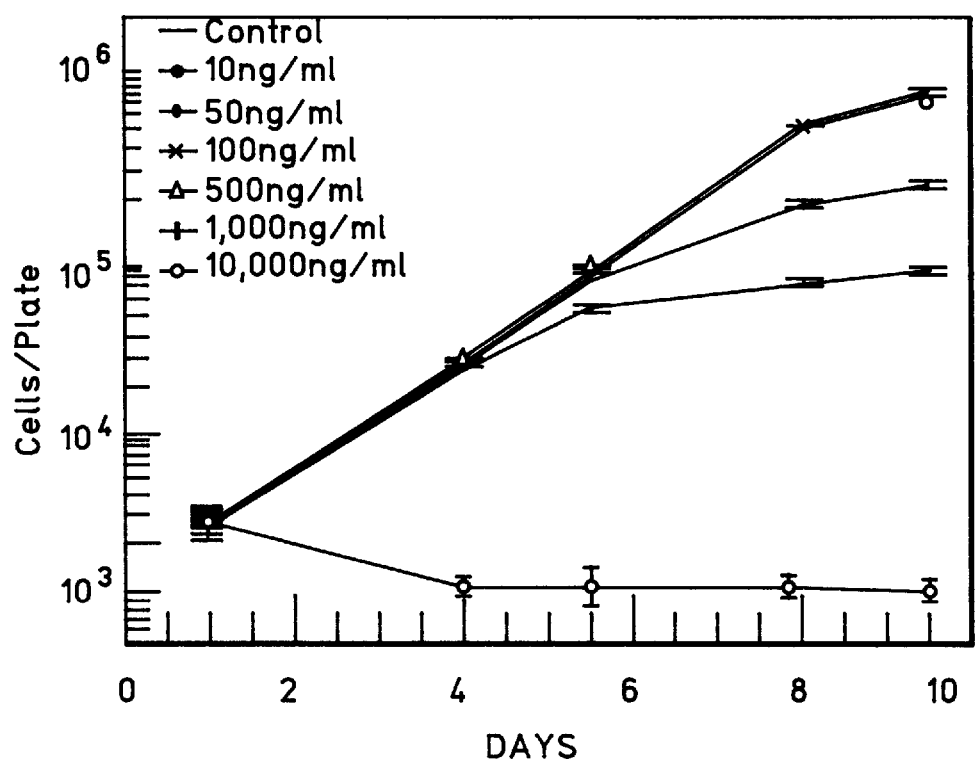
FIG. 12 illustrates results of a DAPI toxicity assay on normal human neonatal foreskin fibroblasts.

The results of this assay are shown in FIG. 12. FIG. 12 shows that while no toxicity occurs at 10 ng/ml, 50 ng/ml, and 100 ng/ml, metabolic toxicity does occur at 500 ng/ml and higher concentrations. The growth rate begins to be affected for 500 ng/ml between days 5 and 8. Thus, for a 5 day experiment, toxicity begins at a concentration of DAPI 10 times greater than that used for nuclear staining.

The second study, a clonal assay, was carried out on 3T3 cells. The cells were grown under the same conditions as for the fibroblast assay. The cultures were begun at 500 cells/plate with 4 replicate plates for each of the 6 DAPI concentrations and control. On day one, over 90% of the colonies were single cells. The cells were cultured for 10 days, rinsed with PBS, and fixed and stained with a mixture of 20% methanol, 10% formalin, and 2% crystal violet in water. The visible clones on each plate were counted and the mean and standard deviation of each set of four are shown in Table II below:

TABLE II

DAPI Clonal Toxicity Assay/3T3 Cell Line

| [DAPI] ng/ml: | 0 | 10 | 50 | 100 | 500 | 1,000 | 10,000 |
|---|---|---|---|---|---|---|---|
| Number of Clones: | 265 | 275 | 283 | 284 | 279 | 315 | 0 |
| Standard Deviation: | ±15 | ±36 | ±24 | ±22 | ±13 | ±39 | ±0 |

These data show no significant difference in clone number until a DAPI concentration of 10,000 ng/ml, at which no clones existed. Under phase contrast microscopy, no attached cells were seen at this dye concentration. This implies that the toxicity for 3T3 cells occurs at a higher concentration than for the normal fibroblasts. These studies, however, are difficult to compare because of the different techniques utilized. Note in particular that at concentrations of 1 $\mu$g/ml and 500 ng/ml in the fibroblast assay the decrease in growth rate was time dependent. This time dependent effect would not be measured in a clonal assay. By the time growth-rate was slowed (day 5), colony size would have been greater than the threshold required for counting and would have no effect. These studies illustrate, however, that DAPI toxicity is not likely to be a limiting problem for scanning cytometry of live cells.

Use of the presently disclosed methodology provides solutions for some of the problems inhibiting the use of images for automated cytometry. For the first time, nuclear recognition accurate and fast enough for fully automated operation has made measurement of $10^4$–$10^5$ attached cells possible. Accurate recognition contributed to identification of the area-dependent photometric error caused by imperfect light sensitivity. The solution to this error, combined with accurate recognition, resulted in DNA content data approaching the precision of flow cytometry. This work represents the realization of one goal for image cytometry: the measurement of nuclei in cell monolayers.

In spite of the improvement in photometric precision over other image cytometry reports, the achievement 2n (or $G_1+M$) coefficients of variation comparable to flow cytometry will probably require improvement in several scanning cytometry components. The magnitude of some of the errors caused by arc lamp instability, narrow depth of field, limited intrascene dynamic range, and photobleaching was presented, along with methods for improvement, in the incorporated dissertation. With the improvements presented herein, scanning cytometry may become as precise a fluorometric tool as flow cytometry.

The use of scanning cytometry on live cells is compelling because cells do not have to be suspended and repeated scanning should allow temporal measurements of a group of cells on a cell-by-cell basis. The scanning cytometer presented here is capable of a scanning interval of 30 minutes on $10^3$–$10^4$ cells. This interval may allow resolution of the major cell cycle phases: $G_0$, $G_1$, S, $G_2$ and M.

The image cytometer itself could affect cell growth through dye toxicity or phototoxicity. The DAPI toxicity assays presented herein show that cell growth is not affected until a dye concentration of 100–500 ng/ml, about 10 times greater than the 10–50 ng/ml required for staining. Shuttered image acquisition, combined with phase contrast autofocus, minimizes the amount of excitation light exposure and limit phototoxicity. The comparison of fifteen autofocus functions referred to herein (and detailed in the incorporated dissertation), yielded two that should be useful for autofocus with phase contrast microscopy. The dose response of cell growth to the excitation light, however, is still under investigation. If phototoxicity is not significant, image cytometry is likely to become a powerful tool for studies involving live cells.

It is also possible to decrease or minimize light intensity via use of a more sensitive camera or other image sensor. Preferably, such a device has high sensitivity, high resolution, and limited geometric distortion. In addition, fiber optic coupling and video output are preferred attributes. The ICCD-1381F Intensified CCD Camera (Video Scope International, Ltd., Washington, D.C.) is one such example of a more sensitive image sensor, which may be applied to either low light level fluorescence or standard low light level analysis/surveillance.

EXAMPLE III

Correction of Photometric Offset Error

FIG. 10 also demonstrates the correction for an error caused by the combination of two image cytometry characteristics: imperfect sensitivity and intensity measured by multiple sensors. This error can be demonstrated by assuming the existence of two nuclei of equal DNA contents and different projected areas, measured by different numbers of sensors. Suppose nuclei n1 and n2 have areas of a1 and a2 pixels respectively. Let it1 and it2 be the average true fluorescence of the smaller subsampled regions of n1 and n2. If is is the intensity lost due to imperfect sensitivity then ip1=it1−is and ip2=it2−is are the average pixel intensities. Because both nuclei have the same DNA content, their true integrated intensities are also equal and a1it1=a2it2. The integrated intensities of n1 and n2 calculated from the image are as follows:

$$I1=a1(it1-is) \text{ and } I2=a2(it2-is) \quad (6)$$

Substituting it2=a1it1/a2 yields I2=a1it1−a2is. Combining equations gives the equation:

$$I1=I2+(a2-a1)is \quad (7)$$

The relative intensities therefore differ by an amount that depends on the difference in area and the amount of unmeasured light per pixel. Nuclei with larger area and the same DNA content have lower integrated intensities. The larger the area, the more the DNA content is underestimated. This dependence on area is exhibited by the negative slope of the area curve in the region of the $G_1$ peak in the uncorrected data. Another effect of the unmeasured intensity is a shift in the uncorrected histogram to the left, resulting in a $G_2$ peak centered at greater than twice the intensity of the $G_1$ peak.

The photometric offset is due largely to imperfect camera sensitivity. This offset also varies with the gain and level settings on the camera and image processor. An indirect method for determining the offset error was utilized for the data shown in FIG. 10. This method is based on the assumption that area is independent of DNA content in the region of the 2n peak. These image objects all have the same DNA content and errors in measuring that content should be random (the mitotic figures are exceptions, see discussion supra). A random relationship to area would yield a zero slope in the area curve in the 2n region. The integrated intensities were corrected by adding back an offset value for each pixel. This constant was assumed to be correct when the slope of area curve in the $G_1$ region became zero. Note that the $G_1$ peak is narrower and taller, suggesting a lower coefficient of variation, and that the left shift of the peaks is corrected.

A second, direct method for measuring the photometric offset should also be possible. Before an experiment, after the proper light intensity, gain, and offset have been determined, a calibration curve using precalibrated neutral density filters could be plotted. The average digital intensity of the shade-corrected flat field image would be plotted as a function of filter transmittance. The y-intercept of this linear function should provide a reasonably accurate system offset measurement that could then be added to each pixel during analysis. The first, indirect method allows data correction even after the image processor and camera settings have been changed while the second, direct method provides a completely data-independent method of correction.

Several other non-trivial improvements in operator-independent image cytometry should be acknowledged, as they are important components of the present invention. For example, the increase in speed will yield results on fixed cells in more reasonable times and improve temporal resolution for live cell studies. The theoretical limit with the image processor used here is about 0.25 s/image, or about an order of magnitude faster than current performance. Another suggestion provided by the present disclosure is the use of additional fluorescent dyes for recognition of other cellular features. The methods described herein for enhancing contrast to improve recognition accuracy are also applicable to other cellular features.

Finally, general application of scanning cytometry to cell smears, histologic sections and cells that grow without contact inhibition, or in matrices, has been advanced by the present invention. While we are continuing to address various aspects of the wide scale implementation of scanning cytometry as a general tool for cell physiology, important components of scanning cytometry have been advanced by the work disclosed herein.

The Arc Lamp Stabilization and Intensity Control System

Arc lamps exhibit short-term flicker, intermediate-term variation, and long-term intensity decay. The short term flicker includes spatial and temporal variations in intensity. The spatial variation is inherent in an arc lamp which produces an effect called arc wander, i.e., the arc moves over time. Such arc wander results in undesirable changes in intensity thus reducing the quality of the magnified image.

Thus, having an arc lamp with smooth spatial and temporal intensity would be an important step in microscopy. The present invention includes an arc lamp stabilization and intensity control system that provides the desired results. Smoothing spatial variations in intensity is achieved via use of a light scrambler, preferably embodied as an optical fiber. In addition, greater light can be applied to a specimen by employing the ellipsoidal reflector of the present invention.

By using the light scrambler, a photodiode can be used to measure average intensity. The photodiode produces an input to a feedback system that varies the current to the arc lamp, i.e., intensity control. The combination of these various elements in a system results in a degree of light source stability previously unattainable with arc lamps.

Figure 13:
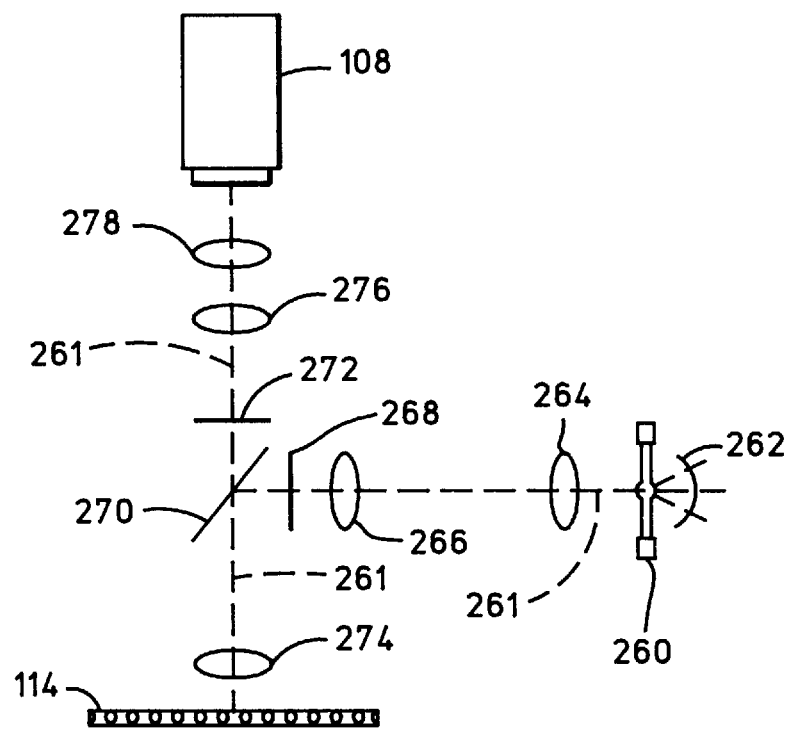
FIG. 13 is a schematic diagram of the optics of an epifluorescent microscope of the prior art.

A schematic of one prior art microscope lighting system is illustrated in FIG. 13. In the following discussion many parts will include a commercial source in parentheses. However, it should be understood that these are currently preferred sources and that other sources and parts may be substituted therefor.

In FIG. 13, an arc lamp 260 (OSRAM HBO 100W/2, Bulbtronics, Anaheim, Calif.) is provided as the light source for the optical components of a microscope (e.g., microscope 102 shown in FIG. 1). The light generated from the arc lamp 260 is indicated at 261. A reflector 262 (Nikon Inc., Garden City, N.Y.) reflects light from one side of the arc lamp 260 back in the direction of the microscope. The direct light from the arc lamp 260, and the light reflected from the reflector 262, is collected by a set of light source collector lenses 264 (Nikon Quartz Collector).

From the light source collector 264, the light travels through a lens 266 (Nikon) (note that the reflector 262 and lens 266 are parts of the standard Nikon Optiphot with Epifluorescence) and an exciter filter 268 (365 DF 12, Omega Optical, Brattleboro, Vt.) to a dichroic mirror 270 (DC 405 LP, Omega Optical). The light is reflected from the mirror 270 so as to travel through an objective 274 (20× phase/fluorite, 85002, Nikon) onto a specimen 114 on the stage 103 (FIG. 1) of the microscope 102.

The magnified image of the specimen 114 then travels back through the objective 274, the dichroic mirror 270 and an emitter filter 272 (485 DF 30, Omega Optical). The image is focused through two video camera projection lenses 276, 278 (TV 1×16, Nikon) and received by the video camera 108.

The resulting image produced in the prior art microscope from the arc lamp light source includes spatial and temporal variations in image intensity that limit the capabilites of image separation as previously described. However, it has been shown that spatial variance in intensity can be reduced by the use of a light scrambler.

Figure 14:
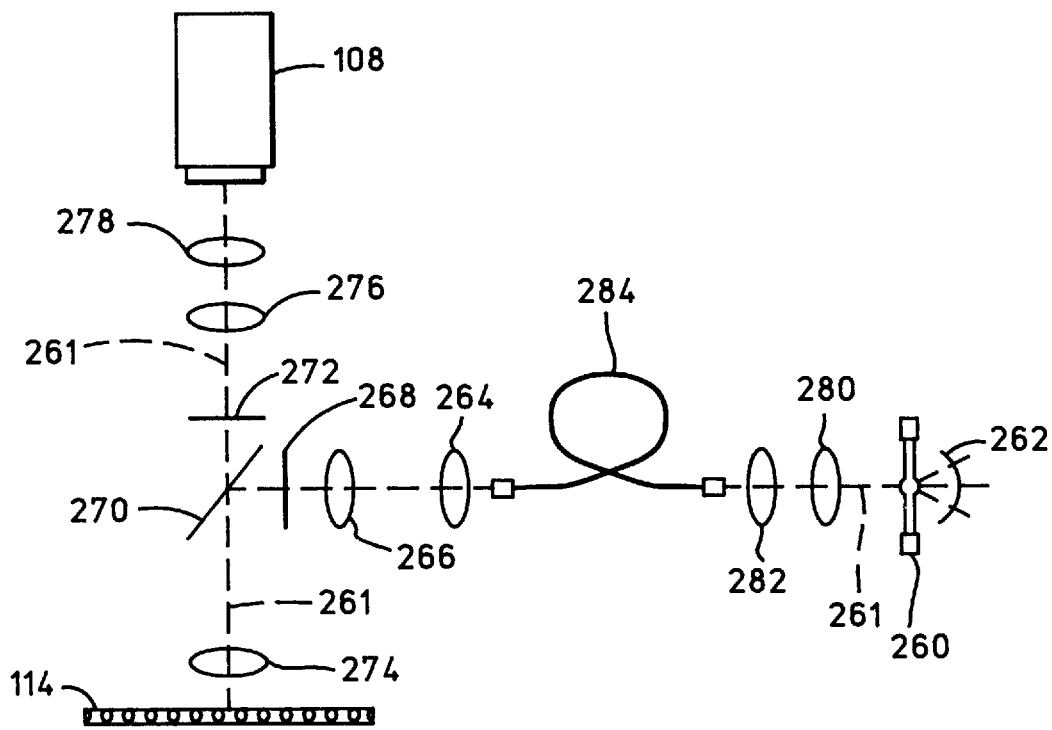
FIG. 14 is a schematic diagram of the optics of the epifluorescent microscope shown in FIG. 13 as modified by a fiber optic scrambler assembly of the prior art.

Turning now to FIG. 14, a light scrambler is shown in a schematic of a second prior art microscope lighting system. The light scrambler comprises three parts that are added to the system of FIG. 13 between the arc lamp 260 and the light source collector lenses 264. First, FIG. 14 differs from FIG. 13 by the insertion of a set of second light source collector lenses 280 after the arc lamp 260. The collector lenses 280 are typically identical to the light source collector lenses 264. Second, a set of fiber optic focusing lenses 282 is added after the collector lenses 280. The fiber optic focusing lenses 282 are typically identical to the light source collector lenses 264, but reversed. Finally, a length of optical fiber 284, for instance, 1 millimeter diameter×1 meter, (77513, with connectors, 77573, Oriel Corp., Stratford, Conn.) is inserted after the focusing lenses 282. The fiber is coiled one or more turns (three turns with the preferred optical fiber) so that the light is randomly reflected, thereby producing a smooth spatial intensity at the light source collector lenses 264. The light from the focusing lenses 282 travels through the remainder of the optical system as discussed with respect to FIG. 13.

The lenses 280, 282 function to collect and focus light into one end of the optical fiber 284. In traveling through the coiled fiber 284 the light 261 is reflected many times off the internal wall of the fiber 284. These multiple reflections scramble the image of the arc light source.

It should be observed that the lenses 262, 280 and 282 form one preferred light scrambling configuration suggested by Technical Video Limited of Woods Hole, Mass., but other configurations may be possible.

Figure 15:
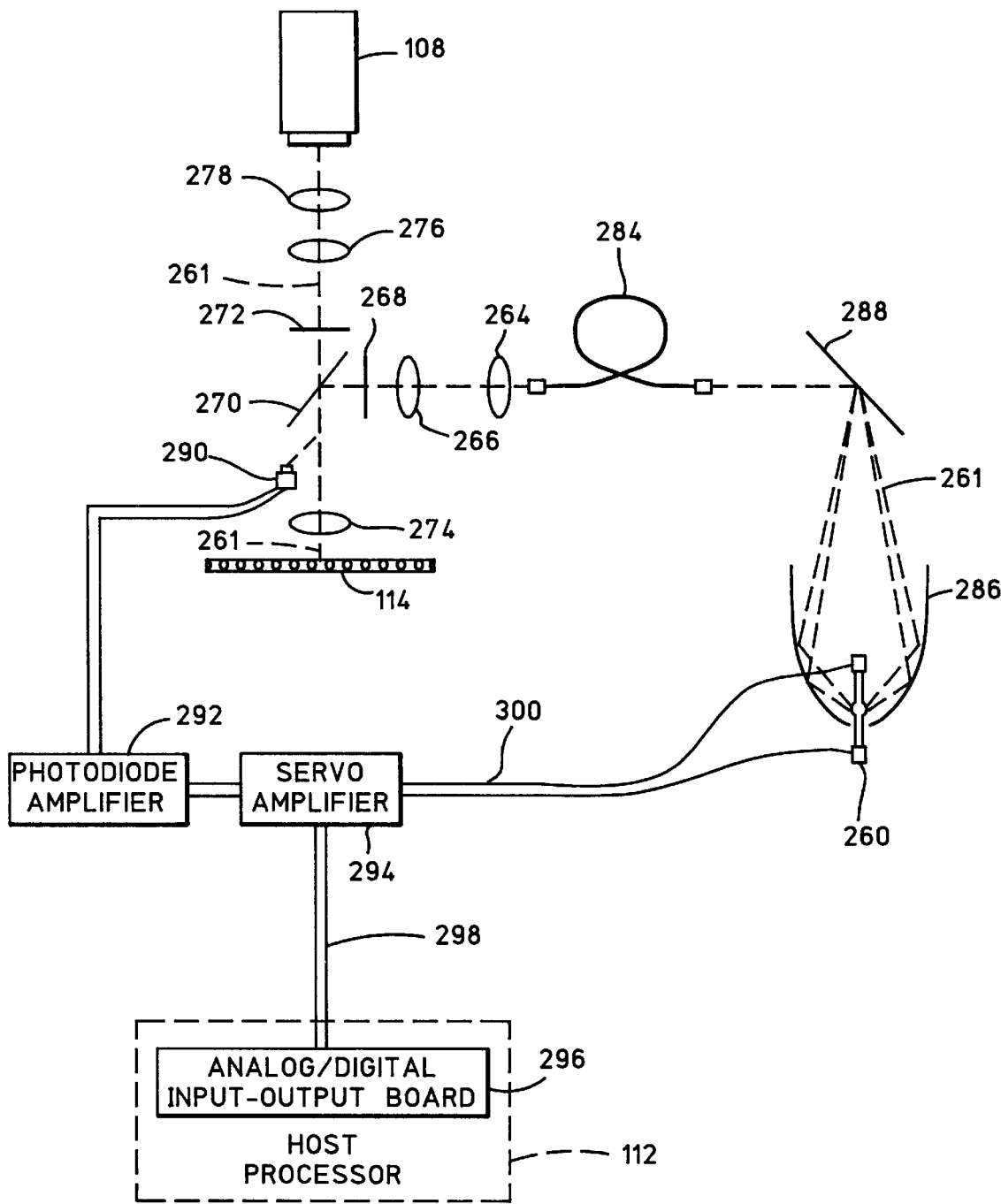
FIG. 15 is a schematic diagram of the arc lamp stabilization and intensity control system of the present invention.

The presently preferred embodiment of the arc lamp stabilization and intensity control system of the present invention is illustrated in FIG. 15. In this system, the arc lamp 260 generates light 261 into an ellipsoidal reflector 286 (Photomax F/2 Reflector with $AlMgF_2$ Coating 60113, Oriel Corp.). The light 261 is then reflected by a dichroic reflector 288 (350–450 nm, 60142, Oriel Corp.) into one end of the optical fiber 284.

Light passes through the optical path previously described with respect to FIG. 14, i.e., onto the specimen 114 and through the objective 274 so that the video camera 108 receives a magnified image of the specimen 114.

Stabilization and intensity control is established through feedback which will now be described. A photodiode 290 (SD-076-12-12-011, Silicon Detector Corp., Camarillo, Calif.) is placed between the dichroic mirror 270 and the objective 274 so as to receive a portion of the light 261. The photodiode 290 is positioned off the optical axis far enough to avoid appearing in the image of the specimen 114. The photodiode 290 produces an electrical signal that is amplified by a photodiode amplifier 292 (which is further described with respect to FIG. 16). The amplified signal is fed to a servo amplifier 294 (preferably the pulse width modulated (PWM) servo amplifier, model 220, available from Copley Controls Corp. of Newton, Mass.) that is controlled by the host processor 112 via an analog-to-digital (A/D) input/output board such as, for example, model DT2801-A from Data Translations, Marlboro, Mass.

In the preferred embodiment, the photodiode amplifier 292 is adjusted to deliver a range of about 0 to 5 volts dependent on the normal intensity range viewed by the photodiode 290. The servo amplifier 294 receives the output of the photodiode amplifier 292 and a reference voltage from the host processor 112. The servo amplifier 294 then alters the current to the arc lamp 260 in such a way as to maintain no, or very little, difference between the output voltage of the photodiode amplifier 292 and the reference voltage. In the presently preferred embodiment, the current across the line 300 is in the range of about 1.5 to 5.5 amperes for a 100 watt arc lamp. This establishes a desired light intensity for the specimen 114.

If intensity is changed from the host processor 112 by specifying a new reference voltage, the servo amplifier 294 will change its output current to alter intensity until the photodiode amplifier 292 output voltage matches the new reference voltage. As the arc lamp 260 changes temperature secondary to the new current, the servo amplifier 294 will maintain constant intensity by changing its output current as required. Also, instability in the intensity of the arc lamp 260 attributed to the arc wander or arc lamp decay will be compensated by the system of the present invention.

Figure 16:
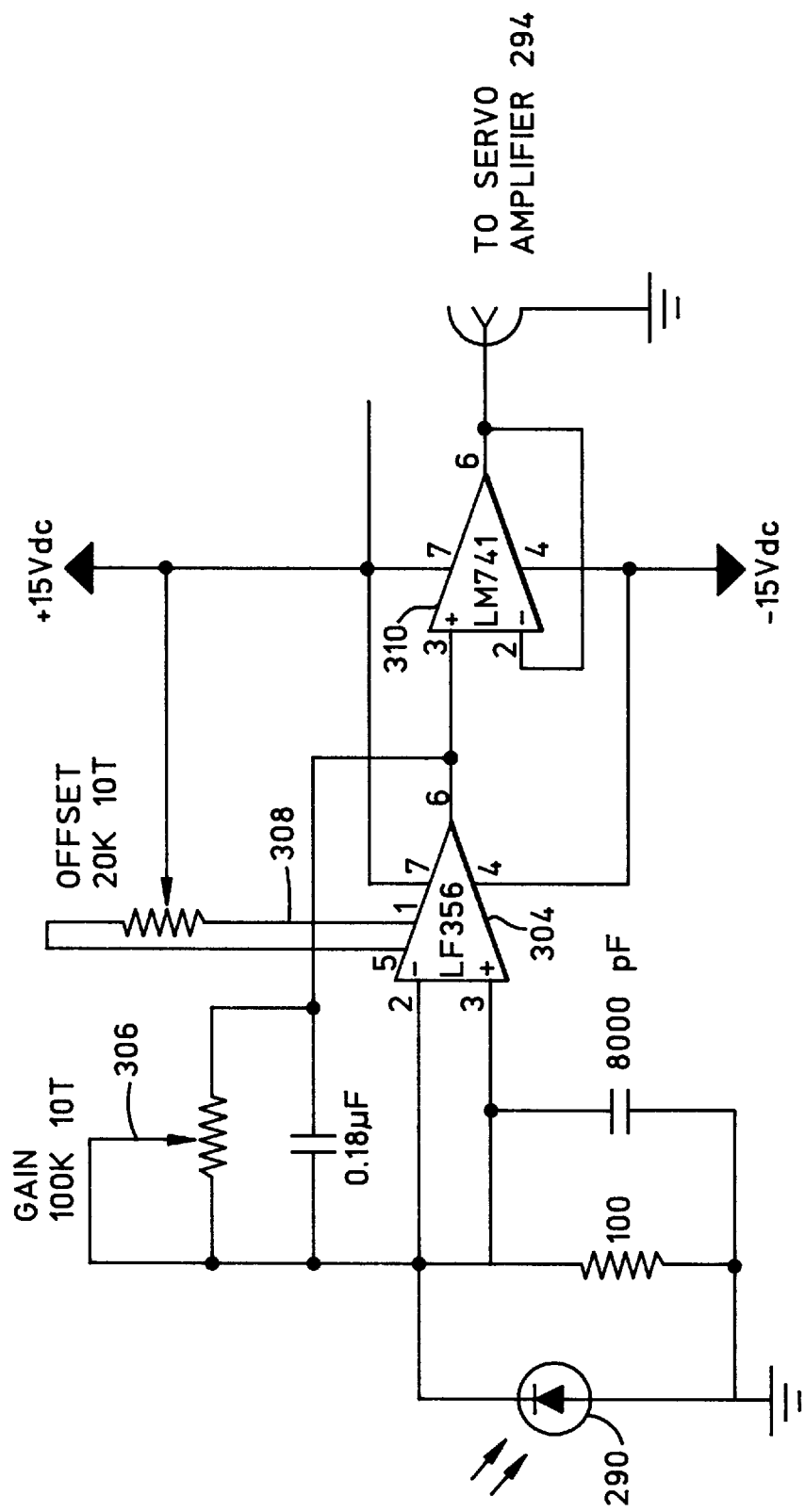
FIG. 16 is a schematic diagram of the photodiode amplifier of FIG. 15.

FIG. 16 illustrates a schematic diagram of the preferred photodiode amplifier 292 (power sources not shown) of the arc lamp stabilization and intensity control system shown in FIG. 15. In FIG. 16, the photodiode 290 produces a current from the light emitted by the arc lamp 260 (FIG. 15). The signal thus generated is amplified by a differential amplifier 304, such as, for example, an LF356 operational amplifier.

The gain of the amplifier 304 is controlled by a potentiometer 306. The potentiometer 306 is adjusted so that the voltage output by the photodiode amplifier 292 falls within the range of servo amplifier input values (FIG. 15). The offset of the amplifier 306 is also controlled by a potentiometer 308. The potentiometer 308 is adjusted so that a threshold photodiode voltage results in about zero voltage output from the amplifier 304.

The output signal of the amplifier 304 is fed to a buffer amplifier 310 and then to the servo amplifier 294 (FIG. 15). The amplifier 310 buffers the differential amplifier 304 from changes in impedance attributed to the servo amplifier 294.

SUMMARY

Although the present invention includes an image cytometer for cell measurement, one skilled in the technology will recognize that there are other applications of the image segmentation described herein. For instance, the present invention could have an application to particle recognition as known in the material sciences.

While the above detailed description has shown, described and pointed out the fundamental novel features of the invention as applied to various embodiments, it will be understood that various omissions and substitutions and changes in the form and details of the device illustrated may be made by those skilled in the art, without departing from the spirit and scope of the claimed invention.

What is claimed is:

1. An imaging system with arc lamp stabilization and intensity control, comprising:

an imaging apparatus for obtaining an image of a magnified object;

an arc lamp for producing light; and the imaging apparatus including an objective through which the light travels to illuminate the object;

means coupled to the arc lamp and to the objective for removing spatio-temporal variation in the light by scrambling the light and adjusting current to the arc lamp in response to intensity of the light at the objective.

2. The imaging system defined in claim 1, wherein the means includes a light scrambler with an optical fiber having a plurality of loops.

3. The imaging system defined in claim 2, wherein the means further includes a photodiode positioned near the objective for detecting the intensity of the light.

4. The imaging system defined in claim 3, wherein the means further includes a photodiode amplifier coupled to the photodiode.

5. The imaging system defined in claim 4, wherein the means further includes a servo amplifier coupled to the photodiode amplifier and to the arc lamp.

6. The imaging system defined in claim 5, wherein the servo amplifier receives a reference signal from a computer.

7. The imaging system defined in claim 6, wherein the light scrambler includes an ellipsoidal reflector positioned near the arc lamp for receiving light from the arc lamp, the optical fiber being positioned to receive light from the ellipsoidal reflector and to provide light to the objective.

8. A microscope system with arc lamp stabilization and intensity control, comprising:

a microscope;

an arc lamp for producing light to illuminate an object to be magnified by the microscope;

the microscope including an objective through which the light travels to illuminate the object;

an ellipsoidal reflector for reflecting light from the arc lamp; and means coupled to conduct light from the ellipsoidal reflector to the objective and coupled to the arc lamp for removing spatio-temporal variations in the light by scrambling the light received from the ellipsoidal reflector and adjusting current to the arc lamp in response to intensity of the light at the objective.

9. The microscope system defined in claim 8, wherein the means includes a light scrambler with an optical fiber having a plurality of loops, the optical fiber being positioned to receive light from the ellipsoidal reflector and to provide light to the objective.

10. The microscope system defined in claim 9 additionally comprising a reflector for reflecting light from the ellipsoidal reflector to the light scrambler.

11. The microscope system defined in claim 10, wherein the means further includes a photodiode positioned near the objective for detecting the intensity of the light from the arc lamp.

12. The microscope system defined in claim 11, wherein the means further includes a photodiode amplifier coupled to the photodiode.

13. The microscope system defined in claim 12, wherein the means further includes a servo amplifier coupled to the photodiode amplifier and to the arc lamp.

14. The microscope system defined in claim 13, wherein the servo amplifier receives a reference signal from a computer.

* * * * *